United States Patent
Sarkas et al.

(10) Patent No.: US 11,672,744 B2
(45) Date of Patent: Jun. 13, 2023

(54) ZINC OXIDE PARTICLES, PHOTOSTABLE UV FILTERS, AND METHODS OF USE THEREOF

(71) Applicant: Nanophase Technologies Corporation, Romeoville, IL (US)

(72) Inventors: Harry W. Sarkas, Shorewood, IL (US); Christopher C. Boffa, Joliet, IL (US)

(73) Assignee: Nanophase Technologies Corporation, Romeoville, IL (US)

( * ) Notice: Subject to any disclaimer, the term of this patent is extended or adjusted under 35 U.S.C. 154(b) by 31 days.

(21) Appl. No.: 17/186,518

(22) Filed: Feb. 26, 2021

(65) Prior Publication Data
US 2022/0000731 A1 Jan. 6, 2022

Related U.S. Application Data

(60) Provisional application No. 63/047,856, filed on Jul. 2, 2020.

(51) Int. Cl.
*A61K 8/27* (2006.01)
*A61K 8/02* (2006.01)
(Continued)

(52) U.S. Cl.
CPC .............. *A61K 8/27* (2013.01); *A61K 8/0241* (2013.01); *A61Q 17/04* (2013.01); *A61K 2800/413* (2013.01); *A61K 2800/522* (2013.01); *A61K 2800/622* (2013.01); *A61K 2800/63* (2013.01); *A61K 2800/651* (2013.01);
(Continued)

(58) Field of Classification Search
None
See application file for complete search history.

(56) References Cited

U.S. PATENT DOCUMENTS

| 2,616,842 A | 11/1952 | Sheer et al. |
| 2,657,149 A | 10/1953 | Iler |

(Continued)

FOREIGN PATENT DOCUMENTS

| EP | 2113528 | 6/2013 |
| EP | 2703351 | 6/2019 |
| WO | 2022/006143 | 1/2022 |

OTHER PUBLICATIONS

Rafla-Yuan, H. et al., "Effects of aluminum doping upon color formation in zinc oxide powders", Journal of Applied Physics, vol. 74, pp. 4685-4690, (1993).
(Continued)

*Primary Examiner* — Dominic Lazaro
(74) *Attorney, Agent, or Firm* — Evan Law Group LLC

(57) ABSTRACT

Zinc oxide particles are prepared as a dry powder through a vapor phase formed by a plasma process, or by introducing defects into stoichiometric zinc oxide particles in a liquid carrier through mechanical stress. The zinc oxide has an O:Zn ratio of at least 0.99, an average particle size of 10 to 300 nm, and a sufficient concentration of oxygen vacancies and zinc vacancies to give a dispersion of the particles in C12-C15 alkyl benzoate an orange to tan color corresponding to a ΔE value of at least 15 in a Dispersion Color Test. The particles contain no aggregates and have no detectable particles 500 nm or larger, on a number-weighted basis.

35 Claims, 3 Drawing Sheets

Adapted from L. Schmidt-Mende and J. L. Macmanus-Driscoll, Materials Today, 10 (5), 40 (2007)

(51) Int. Cl.
A61Q 17/04 (2006.01)
B82Y 5/00 (2011.01)
B82Y 30/00 (2011.01)
B82Y 40/00 (2011.01)

(52) U.S. Cl.
CPC ........... A61K 2800/805 (2013.01); B82Y 5/00 (2013.01); B82Y 30/00 (2013.01); B82Y 40/00 (2013.01)

(56) References Cited

U.S. PATENT DOCUMENTS

| | | |
|---|---|---|
| 2,885,366 A | 5/1959 | Iler |
| 2,938,009 A | 5/1960 | Lucas |
| 3,437,502 A | 4/1969 | Werner |
| 3,849,152 A | 11/1974 | Mimeault |
| 3,900,762 A | 8/1975 | Sheer et al. |
| 3,920,865 A | 11/1975 | Laufer et al. |
| 4,056,494 A | 11/1977 | Kronstein et al. |
| 4,126,591 A | 11/1978 | Kronstein et al. |
| 4,305,853 A | 12/1981 | Kronstein et al. |
| 4,454,288 A | 6/1984 | Lee et al. |
| 4,642,207 A | 2/1987 | Uda et al. |
| 4,732,369 A | 3/1988 | Araya et al. |
| 4,845,054 A | 7/1989 | Mitchener |
| 5,223,250 A | 6/1993 | Mitchell et al. |
| 5,441,726 A | 8/1995 | Mitchnick et al. |
| 5,460,701 A | 10/1995 | Parker et al. |
| 5,486,631 A | 1/1996 | Mitchnick et al. |
| 5,536,492 A | 7/1996 | Mitchnick et al. |
| 5,565,591 A | 10/1996 | Mitchnick et al. |
| 5,756,788 A | 5/1998 | Mitchnick et al. |
| 5,874,684 A | 2/1999 | Parker et al. |
| 5,993,967 A | 11/1999 | Brotzman, Jr. et al. |
| 6,033,781 A | 3/2000 | Brotzman, Jr. et al. |
| 6,214,106 B1 | 4/2001 | Weber et al. |
| 6,869,596 B1 | 3/2005 | Knowland et al. |
| 6,869,956 B2 | 3/2005 | Burke et al. |
| 7,517,513 B2 | 4/2009 | Sarkas et al. |
| 9,139,737 B1 | 9/2015 | Shah et al. |
| 10,183,868 B2 | 1/2019 | McCormick et al. |
| 10,555,892 B1 | 2/2020 | Sarkas et al. |
| 10,590,278 B2 | 3/2020 | Sarkas et al. |
| 2014/0141968 A1 | 5/2014 | Wu et al. |
| 2018/0291210 A1* | 10/2018 | Sarkas ................... A61Q 19/08 |

OTHER PUBLICATIONS

Simpson, J.C. et al., "Characterization of deep levels in zinc oxide", Journal of Applied Physics, vol. 63, No. 5, pp. 1781-1783, (1988).
McCluskey, M.D. et al., "Defects in ZnO" Applied Physics Reviews—Focused review, Journal of Applied Physics, vol. 106, pp. 071101-1-071101-13, (2009).
Schmidt-Mende, L. et al., "ZnO—nanostructures, defects, and devices", Materials Today, vol. 10, No. 5, pp. 40-48, (2007).
Yi, G. et al., "ZnO nanocrystal coated zinc particles degrade dyes in the dark by constantly releasing •$O_2^-$ and $H_2O_2$", The Journal of Physical Chemistry C, vol. 123, pp. 19230-19237, (2019).
Cox, A.J. et al., "An experiment to measure Mie and Rayleigh total scattering cross sections", American Journal of Physics, vol. 70, No. 6, pp. 620-625, (2002).
Gers, R. et al., "Numerical modelling of grinding in a stirred media mill: Hydrodynamics and collision characteristics", Chemical Engineering Science, vol. 65, issue 6, pp. 2052-2064, (2010).
Sarkas, H.W. et al., "The photophysics of environmental protection for preventing premature aging", Technology R&D, Euro Cosmetics, pp. 20-24, (2018).
Berstein, E.F. et al., "Beyond sun protection factor: An approach to environmental protection with novel mineral coatings in a vehicle containing a blend of skincare ingredients", Journal of Cosmetic Dermatology, vol. 19, issue 2, pp. 407-415, (2020).
International Search Report and Written Opinion dated Oct. 26, 2021 for PCT application No. PCT/US2021/039667.
Tamblyn, R.J., "Analysis of energy requirements in stirred media mills", School of Chemical Engineering, College of Engineering and Physical Sciences, The University of Birmingham, pp. 1-178, (2009).
Wada, N. et al., "Mycosporine-like amino acids and their derivatives as natural antioxidants" Antioxidants, vol. 4, pp. 603-646, (2015).
"Specific labeling requirements for specific drug products", Code of Federal Regulations, Title 21, vol. 4, pp. 1-13, (2021).
"Sunscreen drug products for over the counter human use; Amendment to the tentative final monograph; Enforcement policy", Department of Health and Human Services, Food and Drug Administration, Federal Register, vol. 63, No. 204, pp. 56584-56589, (1998).
"Sunscreen drug products for over the counter human use", Code of Federal Regulations, Title 21, vol. 5, pp. 1-3, (2021).
"Sunscreen drug products for over-the-counter human use", Department of Health and Human Services, Food and Drug Administration, Federal Register, vol. 84, No. 38, pp. 6204-6275, (2019).
"Labeling and effectiveness testing; Sunscreen drug products for over-the-counter human use", Department of Health and Human Services, Food and Drug Administration, Federal Register, vol. 76, No. 117, pp. 35620-35665, (2011).
"Labeling and effectiveness testing; Sunscreen drug products for over-the-counter human use", Department of Health and Human Services, Food and Drug Administration, Federal Register, vol. 76, No. 128, p. 38975, (2011).
"Guidance document suncreen monograph", Health Canada, Health Products and Food Branch, pp. 1-22, (2012).
Rafla-Yuan, H. et al., "Optical reflectance of aluminum-doped zinc oxide powders", Journal of Applied Physics, vol. 69, No. 2, pp. 959-964, (1991).
European Search Report dated Jan. 4, 2022 for EP application No. 21183569.9.
Ko, T.S. et al., "ZnO nanopowders fabricated by dc thermal plasma synthesis", Materials Science and Engineering B, vol. 134, pp. 54-58, (2006).
Tsumaki, M. et al., "Size-controlled sub-micrometer spheroidized ZnO particles synthesis via plasma-induced processing in microdroplets", Materials Letters, vol. 166, pp. 81-84, (2016).
Sivkov, A. et al., "Plasma dynamic synthesis and obtaining ultradispersed zinc oxide with single-crystalline particle structure", Advanced Powder Technology, vol. 27, No. 4, pp. 1506-1513, (2016).
Shanenkova, Y. et al., "Plasma dynamic synthesis of ultradispersed zinc oxide and sintering ceramics on its basis by SPS method", IOP Conference Series, Journal of Physics, Conference Series 830, 5th International Congress on Energy Fluxes and Radiation Effects, pp. 1-6, (2017).
Wang, J. et al., "Synthesis, properties and applications of ZnO nanomaterials with oxygen vacancies: A review", Ceramics International, vol. 44, Issue 7, pp. 7357-7377, (2018).
Chen, D. et al., "Influence of defects on the photocatalytic activity of ZnO", The Journal of Physical Chemistry C, vol. 118, Issue 28, pp. 15300-15307, (2014).
Tasker, P.W. et al., "Quenching of luminescence in semiconductors by charged defects", Journal of Physics C: Solid State Physics, vol. 10, pp. 5131-5140, (1977).
"Guidance document sunscreen monograph", Health Canada, Health Products and Food Branch, pp. 1-22, (2012).
Ko, T.S. et al., "ZnO nanopowders fabricated by dc thermal plasma synthesis", Materials Science and Engineering B, vol. 134, pp. 54-58, (2006).
6 pages, mailed Jan. 4, 2022, Application No. 21183569.9, EP.
4 pages, mailed Jan. 18, 2022, Application No. 10-2021-7042724, KR.
5 pages, mailed Jan. 14, 2022, Application No. 21183569.9, EP.
7 pages, mailed Aug. 23, 2022, U.S. Appl. No. 17/186,518, US.
5 pages, mailed Sep. 15, 2022, Application No. 21183569.9, EP.
21 pages, mailed Nov. 9, 2022, U.S. Appl. No. 17/186,518, US.

* cited by examiner

Adapted from L. Schmidt-Mende and J. L. Macmanus-Driscoll, Materials Today, *10* (5), 40 (2007)

ZINC OXIDE PARTICLES, PHOTOSTABLE UV FILTERS, AND METHODS OF USE THEREOF

BACKGROUND

Zinc oxide is a wide band-gap semiconductor with a reported band gap of 3.3-3.4 eV, making it an ideal candidate for a wide variety of applications including use as a primary white pigment [1,2], a variety of electronic, optoelectronic, and magneto-optic devices [3,4], and as a broad spectrum UV filter for topical sunscreen applications [5-7,43-45]. The use of zinc oxide in sunscreen has received particular attention recently as one of only two GRASE (Generally Regarded as Safe and Effective) sunscreen actives in the FDA proposed rule [45]. Pigmentary particles typically have larger sizes (from greater than 300 nm to about 16 µm) in order to scatter visible light, while particles used in UV filters typically have small particle sizes (300 nm or less) in order to avoid scattering light.

As a primary pigment, zinc oxide possesses the undesirable characteristic of developing a yellow coloration when subjected to mechanical grinding or high doses of UV radiation in vacuo. Any deviation from pure white is commercially unacceptable for use as a pigment, and traditionally was unacceptable when used as a UV filter or in cosmetic applications. The origin of this trait was extensively studied using reflectance spectroscopy on large pigmentary sized particles by Cordaro,[1] who attributed the origin of the coloration to the formation of oxygen vacancies in zinc oxide and went on to extensively characterize the intrinsic defect levels in bulk single crystal zinc oxide [2]. The studies on pigmentary particles revealed that oxygen vacancy defects could be created through both grinding (which induced mechanical damage and the associated disorder) and through addition of excess zinc (via heat treatment in the presence of zinc vapor), but rapid cooling had little effect on the observed reflectance spectrum of the powder. The work also disclosed methods for preventing the formation of oxygen defects and the associated coloration through doping with selected dopants having oxygen rich oxides in comparison to ZnO. This doping method leads to the elimination of oxygen defects and preserves the white color of the pigment. While this method is suitable for large pigmentary sized particles, it is not practical for UV filter particles which are categorized as drug actives in some jurisdictions, and are required to be delivered at USP level purities, severely limiting the amounts of dopants which may be added.

The characterization of the intrinsic defect levels has continued and has been presented in summary [4]. The types of native defects in zinc oxide are presented in FIG. 1. The defect types are described using Kröger-Vink notation, where Zn=zinc, O=oxygen, i=interstitial site, V=vacancy, a dot indicates a positive charge, a double dot indicates a double positive charge, a prime indicates a negative charge, a double prime indicates a double negative charge, and x indicates no charge. The native donor defects in zinc oxide are the electron donor defects $Zn_i^{\bullet\bullet}$, $Zn_i^{\bullet}$, $Zn_i^{x}$, $V_o^{\bullet\bullet}$, $V_o^{\bullet}$ and the electron acceptor defects $V_{Zn}^{''}$, and $V_{Zn}^{'}$.

Zinc oxide particles both absorb and scatter UV radiation, with the former playing a larger role as particle size decreases. The absorption of UV radiation in inorganic UV filters including zinc oxide results in the formation of electron-hole pairs known as excitons. Excitons are known to react with molecular oxygen through an electron transfer reaction to produce superoxide anion radicals. Superoxide anion radical is a highly reactive and aggressive species responsible for the formation of a variety of reactive oxygen species, including hydroxyl radical (OH.), lipid alkoxy radicals, lipid peroxyl radicals, singlet oxygen and nitric oxide. These species can initiate or participate in chain reactions and contribute to detrimental effects on skin health. Such reactions may be impeded by sequestering the charge carriers created from UV absorption through targeted surface treatments [30,31] or through quenching of the exciton species.

Defects may be introduced into zinc oxide to quench excitons. One method of introduction of defects for quenching excitons is described in U.S. Pat. No. 6,869,596 to Knowland et al. Luminescent traps or killer sites were introduced into zinc oxide particles smaller than 200 nm by thermal reduction using hydrogen to remove oxygen. The introduction of traps serves the purpose of trapping electrons and holes created upon excitation of the zinc oxide particles with UV radiation. The particles were believed to contain excess $Zn^{2+}$ ions within the absorbing core were demonstrated to impart some reduction in photocatalytic effect.

SUMMARY

In a first aspect, the present invention is zinc oxide particles. The particles have an O:Zn ratio of at least 0.99, an average particle size of 10 to 300 nm, and a sufficient concentration of oxygen vacancies and zinc vacancies to give a dispersion of the particles in C12-C15 alkyl benzoate an orange to tan color corresponding to a ΔE value of at least 15 in a Dispersion Color Test. The particles contain no aggregates and have no detectable particles 500 nm or larger, on a number-weighted basis.

In a second aspect, the present invention is zinc oxide particles having average particle size of 10 to 300 nm. The particles are stoichiometric zinc oxide, the particles have a ΔE value at most 10 in the DPPH Photocatalytic Stability Test, and the particles have a ΔE value at least 15 in the Dispersion Color Test.

In a third aspect, the present invention is coated particles, comprising (a) zinc oxide particles, and a silica coating on the zinc oxide particles. The zinc oxide has (i) an O:Zn ratio of at least 0.99, and (ii) a sufficient concentration of oxygen vacancies and zinc vacancies to give a dispersion of the particles in C12-C15 alkyl benzoate an orange to tan color corresponding to a ΔE value of at least 15 in a Dispersion Color Test. The coated particles have an average particle size of 10 to 300 nm. The particles contain no aggregates and have no detectable particles 500 nm or larger, on a number-weighted basis.

In a fourth aspect, the present invention is coated particles, comprising (a) zinc oxide particles, (b) an organic moiety-containing coating, on the zinc oxide particles. The zinc oxide particles have (i) an O:Zn ratio of at least 0.99, and (ii) a sufficient concentration of oxygen vacancies and zinc vacancies to give a dispersion of the particles in C12-C15 alkyl benzoate an orange to tan color corresponding to a ΔE value of at least 15 in a Dispersion Color Test. The coated particles have an average particle size of 10 to 300 nm. The particles contain no aggregates and have no detectable particles 500 nm or larger, on a number-weighted basis.

DEFINITIONS

The term "particle size" means the average diameter of the image of the particle as viewed by electron microscopy.

The term "particle size" is used in this manner unless otherwise stated. The term "average particle size" means the average of the particle sizes of a collection of particles or that calculated using a spherical model from the specific surface area of particles measured in $m^2/g$ determined using the Brunauer-Emmett-Teller (BET) method consistent with fully-dense particles. The terms "powder" and "particles" are used interchangeably.

The term "stoichiometric" means a composition of zinc oxide having a ratio of O:Zn (referred to as "n") of ≥0.99. This is determined by any mass gain features showing a distinct inflection point with an onset above 400° C. during thermogravimetric analysis under an oxygen atmosphere, and may be calculated assuming all mass gain is oxygen. Preferably, n≥0.999, determined by the lack of any mass gain features showing a distinct inflection point with an onset above 400° C. during thermogravimetric analysis under an oxygen atmosphere.

The term "surface treatment" and "surface coating" are used interchangeably. Furthermore, the term "zinc oxide UV filter" means zinc oxide having an average particle size of at most 300 nm.

The terms "photostable", "photocatalytically stable" and "super-photostable" all refer to the reduction or elimination of the same property of zinc oxide, the chemical reactivity of excitons produced by light absorption. The terms each refer to a different degree of reduction of reactivity, with "super-photostable" being the least reactive and "photostable" being the most reactive, with each having a separate test, one more sensitive than the next. The test to determine if a zinc oxide powder is photostable is described in U.S. Pat. No. 9,139,737, the test for photocatalytically stable is described below, and the test for super-photostable is described in US Patent Publication, Pub. No. 2018/0291210.

The phrase "organic moiety-containing coating" means a surface coating containing —$CH_3$ and/or —$CH_2$— moieties. Examples include particles surface treated with silanizing agents, particles coated with propylsilsesquioxane/dimethiconol/silicate crosspolymer, particles surface treated with a plant-based phosphatide, and particles surface treated by esterifying fatty alcohols or polyglyceryl (polyol) compounds. These surface coatings and treatments may be used to make the particles hydrophobic.

DETAILED DESCRIPTION

Figure 1:
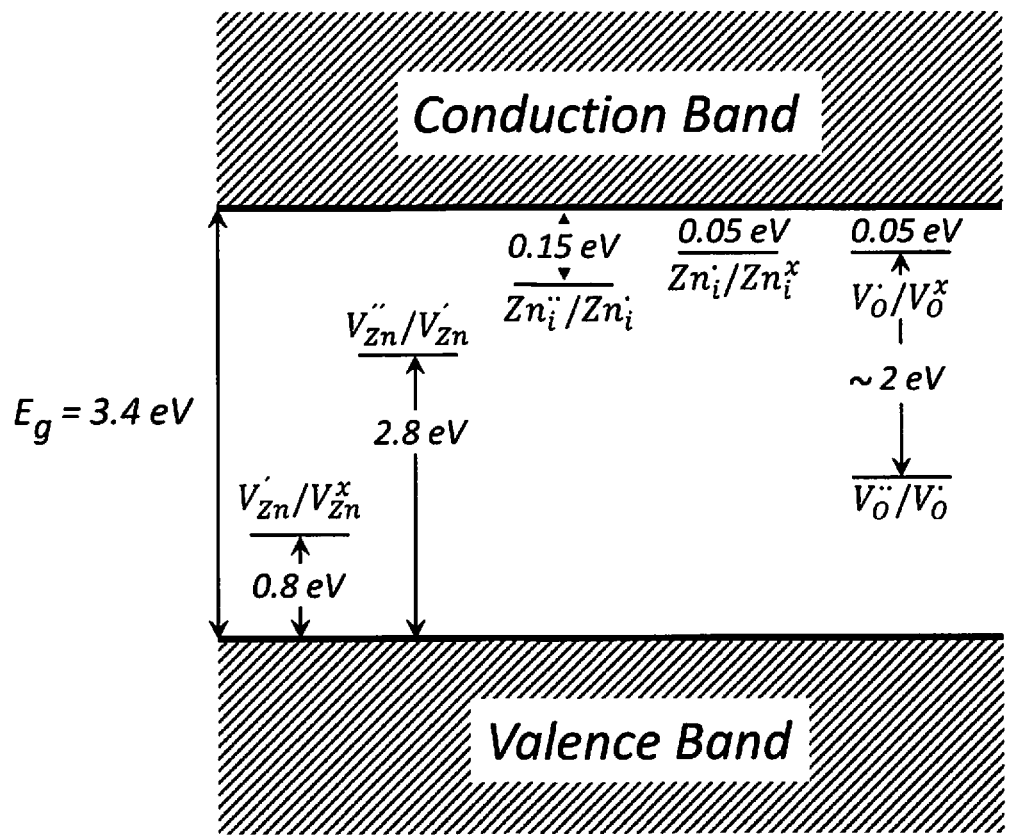
FIG. 1 is a band diagram illustrating the energy levels of defects in ZnO.

The compositions of Knowland et al. are formed by thermal reduction in hydrogen at elevated temperature resulting in the removal of oxygen, and therefore are non-stoichiometric with excess zinc. Such zinc oxide compositions may be identified using thermogravimetric analysis, showing a weight gain in air starting above 400° C. caused by the re-oxidation of the particles. It has been reported [9] that particles of analogous overall composition (described as Zn/ZnO core shell particles) generate free radicals and other reactive oxygen species in the dark. It was confirmed through a free radical test carried out in the dark that the particles of Knowland et al. share this behavior of generating free radicals in a dark environment. The generation of free radicals makes these particles less desirable for use on skin.

The present invention makes use of zinc oxide particles which are stoichiometric, do not contain significant aluminum or transition metal dopants, have an average particle size of 10 to 300 nm, and which contain a sufficient concentration of defects to quench excitons making the particles photostable and photocatalytically stable. The optional further addition of one or more coatings improves the photostability and photocatalytic stability, and allows for improved compatibility with cosmetic formulations. Although the concentration of defects results in a characteristic orange to tan color when dispersed in a liquid carrier, the color has recently become commercially acceptable for cosmetic formulations due to changes in consumer taste. Without wishing to be bound by theory, it is believed that the photocatalytic stability and color result from a threshold concentration of defect states which are responsible both for the color through defect state absorption and for the low photocatalytic activity through exciton trapping. The yellow aspect of such coloration has been attributed to oxygen vacancy defects. Since the particles are stoichiometric ZnO, it may be surmised that the electron donating oxygen vacancy defects present in the particles do not result from the presence of excess zinc atoms, but rather from atomic disorder together with a balance of electron acceptor zinc vacancy defects. The particles of the invention are also non-pigmentary in particle size (that is, an average particle size below 300 nm), and therefore do not substantially scatter visible light. This allows them to be used without imparting significant color when applied to the skin and actually somewhat improving the aesthetic character of formulas containing the particles relative to those containing conventional white zinc oxide.

Preferably, the particles have an average particle size of at most 300 nm, including an average particle size of at most 100, 200, and 300 nm, more preferably an average particle size of 10 nm to 200 nm, most preferably an average particle size of 15 nm to 200 nm, such as 20, 30, 40, 50, 60, 70, 80, 90, 100, 110, 120, 130, 140, 150, 160, 170, 180, 190, and 200 nm. Pigmentary sized (an average particle size >300 nm for zinc oxide) UV absorbing particles are generally characterized by sufficiently low absorption coefficients in the wavelength region 290-400 nm that their practical use in UV protective compositions is excluded because they do not provide sufficient SPF at normal concentration levels. Furthermore, when the particle size is less than 10 nm, the particles are unable to efficiently quench excitons regardless of the concentration of vacancies, because the effective exciton radius in zinc oxide is large enough to extend out of the particles. Such small particles will not be photocatalytically stable.

Agglomerates are defined as collections of weakly bound particles bound by electrostatic interactions. Aggregates are defined as particles bound by strong interactions such as covalent or ionic bonding. The two can be distinguished using by dispersing the particles using low intensity mixing combined with ultrasonication followed by detection and particle size analysis using laser light scattering as described in ISO 13320:2009 (Particle size analysis—Laser diffraction methods). Agglomerates will be broken down revealing their constituent particles while aggregates will remain at the nominal aggregate size and be detected as such. Analyzers suitable for dispersing powders for measurement and determining particle size distributions by this method are the Horiba LA910, the Horiba 960, or equivalents. Preferably, the zinc oxide particles of the invention contain no aggregates and have no detectable particles 500 nm or larger, on a number-weighted basis. The presence of such aggregates results in scattering of both visible and UV light, give the product both poor aesthetics and a reduced absorption of UV light. If the particles to be analyzed are dispersed in a fluid other than isopropanol, they must first be diluted with isopropanol. Dry powders must first be dispersed into isopropanol before analysis.

Preferably, the particles are stoichiometric, that is the zinc oxide particles have a ratio of O:Zn (referred to as "n") of ≥0.99. This is determined by any mass gain features showing a distinct inflection point with an onset above 400° C. during thermogravimetric analysis under an oxygen atmosphere, and may be calculated assuming all mass gain is oxygen. Preferably, n≥0.999, determined by the lack of any mass gain features greater than 0.02% showing a distinct inflection point with an onset above 400° C. during thermogravimetric analysis under an oxygen atmosphere. Thermogravimetric analysis of the particles of Knowland et al. in an oxygen environment will lead to a distinct and characteristic gain in mass resulting from the re-oxidation of the particles once a sufficient temperature is reached. Zinc oxide containing excess oxygen is not stable to mild heating.

Particle stoichiometry is determined using thermogravimetric analysis performed under an atmosphere of pure oxygen in the range 25° C. to 800° C. at scan rates of 10° C./minute to 20° C./minute in a platinum pan. A suitable instrument has a precision of 0.01%. Suitable instruments include TA Instruments Q Series 50 TGA Analyzer or equivalent instruments. For the purpose of analysis to determine stoichiometry, the baseline sample mass is taken as that at a temperature beyond that of mass loss due to gas desorption for dry, uncoated powders, or beyond that of ignition due to coating chemistry (in the case of dry, coated powders) or beyond that of ignition due to solvent and/or dispersant (in the case of coated powders or dispersions). This baseline point is taken to be reflective of the base zinc oxide composition.

The combination of being stoichiometric, together with orange to tan color when dispersed in a liquid carrier of sufficient depth as described below, means that the ZnO particles comprise oxygen vacancy defects ($V_o^{\cdot\cdot}$ and/or $V_o^{\cdot}$) and the zinc vacancy defects ($V_{Zn}''$ and/or $V_{Zn}'$), in substantially the same number, to provide substantial exciton quenching, so that the particles are photocatalytically stable. The stoichiometric zinc oxide is a non-pigmentary particle having low photocatalytic activity that is stoichiometric, in which the low photocatalytic activity is due to a sufficient concentration of charge-balanced intrinsic defects (that is, balanced oxygen vacancies and zinc vacancies) that can serve as exiton traps, and are in a sufficient concentration for identification by having a color past a threshold level of darkening.

The photocatalytic stability of zinc oxide (ZnO) is measured using the test described below. This test is referred to as the "DPPH Photocatalytic Stability Test." First, 0.025 g±0.001 g of ZnO powder on an actives basis is added to six 50 mL disposable plastic beakers. 0.0125% DPPH (di(phenyl)-(2,4,6-trinitrophenyl) iminoazanium, also referred to as diphenylpicrylhydrazyl; CAS Number 1898-66-4) is prepared in BCS (ethylene glycol butyl ether) solution. 19.975 g±0.001 g of 0.0125% DPPH in BCS solution is added to each beaker containing zinc oxide powder. In the case of zinc oxide actives being tested from a dispersion, 0.025 g±0.001 of zinc oxide actives are added from dispersion of known zinc oxide content to six 50 mL disposable plastic beakers. A nominal 0.0125% DPPH solution is prepared in BCS (ethylene glycol butyl ether) where the concentration of BCS is adjusted in a quantity sufficient manner to compensate for the liquid dispersion carrier and any other excipient ingredients in the zinc oxide containing dispersion. 19.975 g±0.001 of the adjusted nominal 0.0125% DPPH in BCS solution is added to each beaker containing zinc oxide dispersion. Samples are mixed thoroughly with a glass stir rod, and each beaker is sonicated for 60 seconds, ensuring the particles are well-dispersed throughout the solution. After sonication, the sample is transferred to a labelled scintillation vial.

The pre-irradiated samples are measured on a Konica Minolta colorimeter CM-600D Colorimeter or suitable equivalent colorimeter calibrated using a NIST traceable white tile. After taking the measurements, the samples are irradiated. The test mixtures are exposed to UV light in a Q-Labs QUV weatherometer using UVB bulbs at 1.28 $Wm^{-2} s^{-1}$ at a constant temperature of 50° C. for exactly 5.5 minutes. Finally, the post-irradiated samples are measured on the colorimeter. Photocatalytic stability following UV exposure is indicated by the persistence of the purple color due to the absorption band of the dye at 520 nm. Photocatalytic stability may be expressed as the total color change relative to a standard (ΔE in L*a*b* color space) for a stated UV exposure time. ΔE is calculated from the following expression, as per the CIE76 definition:

$$\Delta E = \sqrt{(L_2^* - L_1^*)^2 + (a_2^* - a_1^*)^2 + (b_2^* - b_1^*)^2}$$

where $L_2^*$, $a_2^*$, and $b_2^*$ are the color coordinates of test mixture post irradiation and where $L_1^*$, $a_1^*$, and $b_1^*$ are the initial color coordinates of test mixture prior to irradiation. Data is reported as the average ΔE value of the six samples. A particle is photocatalytically stable if ΔE≤10 in the above photocatalytic stability test. In DPPH Photocatalytic Stability Test, preferably the particles have a ΔE≤9, 8, 7, 6, 5 or 3, such as ΔE=1 to 10.

The color of zinc oxide (ZnO) is measured using the test described below. The zinc oxide powder has a sufficient concentration of vacancy defect to have substantial exciton quenching (that is, the powder is photocatalytically stable) if it has a ΔE value of at least 15 in the following test. This test is referred to as the "Dispersion Color Test". A carrier solution of 4.30±0.1% Hostaphat KW 340D (INCI Name: Triceteareth-4 Phosphate) in Finsolv TN (INCI Name: C12-15 Alkyl Benzoate) is first prepared. For powder samples, 3.00±0.01 g of zinc oxide powder on an actives basis is added to a scintillation vial and diluted to a total of 10.00±0.01 g with carrier solution. For dispersion-based samples where the liquid carrier is known to have a Gardner Number of 2 or less, 3.00±0.01 g of zinc oxide on an actives basis from a dispersion of known zinc oxide content are added to a scintillation vial and diluted to 10.00±0.01 g with pure Finsolv TN. Color may be expressed as the total color difference relative to a standard (ΔE in L*a*b* color space). ΔE is calculated from the following expression, as per the CIE76 definition:

$$\Delta E = \sqrt{(L_2^* - L_1^*)^2 + (a_2^* - a_1^*)^2 + (b_2^* - b_1^*)^2}$$

where $L_2^*$, $a_2^*$, and $b_2^*$ are the color coordinates of test sample and where $L_1^* = 99.47$, $a_1^* = -0.16$, and $b_1^* = -0.17$ and correspond to the color coordinates of a white reference tile.

In the Dispersion Color Test, preferably the have a ΔE value of at least 16, 17, 19, 20 or 25, such as a ΔE=15 to 26.

Preferably, the particles do not contain chromium or manganese, which may be determined by elemental analysis. Preferably, the zinc oxide is not doped with silicon or aluminum, which may be confirmed by the color of the zinc not being pure white.

The stoichiometric zinc oxide particles may be prepared as a dry powder through a vapor phase formed by a plasma process using a very high cooling rate, in an environment containing sufficient oxygen to ensure a stoichiometric product. When present as a dry powder, the zinc oxide particles will appear white due to light scattering, even though the actual color of the particles will become apparent when wetted with a liquid carrier, in the form of a dispersion. Alternatively, stoichiometric zinc oxide particles and powder containing defects may be prepared by introducing defects into stoichiometric zinc oxide particle in a liquid carrier through mechanical stress.

Plasma-based particle production methods are well suited to produce the stoichiometric zinc oxide particles [10-16], particularly with the methods described in U.S. Pat. Nos. 5,460,701 and 5,874,684. The method described therein will be referred to as "transferred arc physical vapor synthesis". In these processes, zinc vapor is generated by a transferred arc in a geometry where the magnetic fields of the cathodic and anodic plasma jets produce a projected merged plasma jet of high velocity that contains saturated vapor of the product precursor. The velocity of this plasma jet leads to rapid cooling in a non-equilibrium process. This vapor becomes supersaturated and forms into particles via a condensation nucleation process in which the condensing particles are exposed to oxygen-containing gas to complete the oxidation reaction. The oxidant may further be used to concomitantly dilute the emerging zinc oxide particle stream via micro-mixing to control particle size. This dilution process, which generates a zinc oxide aerosol, may be used to quench the emerging particle stream and may be used to control annealing, oxidation, primary particle growth, and particle coalescence. This zinc oxide aerosol is finally mixed with diluent/transport gas which transports the aerosol to a collector where the product is collected as an electrostatically bound powder consisting of weak agglomerates.

The process factors described in U.S. Pat. Nos. 5,460,701 and 5,874,684 that influence particle size also affect extent of oxidation and defect concentration. Arc power influences both the plasma jet temperature and the zinc atom concentration in the plasma through vaporization rate of the precursor. The rate of introduction of oxidant quench gas and the associated position along the emerging arc jet relative to its position of origin influence the zinc/oxygen atomic ratio, the rate of oxidation, average particle size, and formation of defects. Finally, the rate of introduction of transport gas further influence the rate of oxidation and formation of defects.

In these types of plasma processes, only the hexagonal zincite crystal structure (also referred to as the wurtzite crystal structure) is formed. This structure is a relatively open one which can support a variety of intrinsic defect states [4]. Rapid cooling may be used to "freeze" varying levels of atomic disorder into the zincite crystal structure and control the concentration of defect states as particles are produced. Under certain combinations of process factors, powders are produced which display coloration which can be attributed to the presence of crystal defects. Under certain combinations of process conditions, this coloration may be associated with the presence of excess zinc atoms indicating incomplete oxidation, which is undesirable. Such undesirable materials are sub-stoichiometric zinc oxide which necessarily will display a mass gain showing a distinct inflection point with an onset above 400° C. when measured by thermogravimetric analysis under an oxygen atmosphere. Under different isolated and selected combinations of process conditions, which may be identified through empirical process mapping (that is, by testing different process conditions and testing the product produced), stoichiometric zinc oxide is formed which display deep orange to tan coloration when dispersed in nonaqueous liquids. Example 1, below, provides one set of such conditions. A desirable zinc oxide product simultaneously satisfies the criteria of (1) $\Delta E \geq 15$ in the Dispersion Color Test, (2) $\Delta E \leq 10$ in the DPPH Photocatalytic Stability Test, (3) an average particle size of 10-300 nm, and (4) are stoichiometric with respect to zinc and oxygen ratio.

The stoichiometric zinc oxide particles may also be prepared in a dispersion, preferably in a non-aqueous liquid medium, through the application of sufficient mechanical stress to induce balanced donor and acceptor defects in stoichiometric zinc oxide. Stoichiometric composition in these cases are verified by the absence of mass gain related to oxidation as previously specified relative to the baseline mass established following the ignition of all liquid carriers and surface treatments. Mechanical stress may be applied using a variety of methods, preferably with stirred media mills. The mechanical stress used to create atomic disorder resulting in a sufficient concentration of defects may be applied to any stoichiometric zinc oxide to enhance the concentration of radical trapping defects. The effects of hydrodynamic parameters and collision characteristics associated with fluid type; media size, shape, and composition; and specific energy input have been extensive taught with respect to media milling in general [39,40]. This process may proceed with or without mechanical comminution to reduce particle size, by controlling the size of the milling media. In the latter case, selecting a media size that is large enough so that the practical terminal particle size that may be achieved through comminution exceeds that of the starting average particle size of the powder to be processed, will avoid reducing particle size. The milling is carried out until the particles contain a sufficient concentration of defects to quench excitons making the particles photocatalytically stable, by testing the zinc oxide to determine that $\Delta E \geq 15$ in the Dispersion Color Test. Stoichiometric zinc oxide generated in this manner also simultaneously satisfies the criteria of (1) $\Delta E \geq 15$ in the Dispersion Color Test, (2) $\Delta E \leq 10$ in the DPPH Photocatalytic Stability Test, (3) average particle size of 10-300 nm, and (4) are stoichiometric with respect to zinc and oxygen ratio. Even though the stoichiometric zinc oxide is prepared in a dispersion, the liquid medium may be removed by evaporation to obtain a dry powder.

The zinc oxide may be surface treated or coated using an inorganic oxide in order to further reduce photocatalytic activity of the particles. Such surface coatings also prevents dissolution of zinc into the formulations (Zn(II) ion leakage), which can cause emulsion destabilization or formation of precipitates. Methods of applying surface treatments are well known. Preferred oxides for surface treatment are silica [18-20] and alumina [19]. Such silica and alumina coatings do not affect the color in the Dispersion Color Test. Inorganic surface treatments may be applied at 0.5%-40% of the mass of the zinc oxide particle with the preferred range being 2.0%-20% of the mass of the particle and is adjusted based on the particle specific surface area with larger values of specific surface area typically requiring higher levels of surface treatment. Preferably, the stoichiometric zinc oxide is first surface treated using an inorganic oxide before a further surface treatment or coating described below.

The zinc oxide particles may be coated with one or more organic moiety-containing coatings in order to increase the hydrophobicity of the powders. Such coating and surface treatments typically do not affect the color in the Dispersion Color Test. Such coating and surface treatments may be applied uncoated particles or particles coated with an inorganic oxide.

The zinc oxide may be surface treated with a silanizing agent. The silanizing agent may be applied to the surfaces of particles either in the raw state or after being first surface treated using an inorganic oxide. The silanizing agent may be any substance that provides functionalized polysiloxanes on the surface of the particles. Examples of suitable silanizing agents are well known [21-32] and include reactive silicone and silane hydrophobizing surface treatments (for example, triethoxycaprylylsilane, octadecyltriethoxysilane, hydrogen dimethicones (CAS Numbers 68037-59-2/69013-23-6/70900-21-9) and CAS Number 69430-47-3 (Siloxanes and Silicones, di-Me, reaction products with Me hydrogen siloxanes and 1,1,3,3-tetramethyldisiloxane)). The slianizing surface treatments serve to hydrophobized the particles in order to maintain them in the oil phase of UV protective topical preparations and impart water resistance.

Preferably, the zinc oxide particles are coated using crosspolymers described in US Patent Publication, Pub. No. 2018/0291210, such as propylsilsesquioxane/dimethiconol/silicate crosspolymer which have been demonstrated to further suppress UV induced free radical generation of zinc oxide particles thereby allowing for enhancement of antioxidant activity and suppression of free radicals generated in the skin upon UV exposure, as compared to typical zinc oxide powders. Zinc oxide particles having this coating are super-photostable. US Patent Publication, Pub. No. 2018/0291210 describes a test for photostability and the criteria for determining if a zinc oxide powder super-photostable.

The zinc oxide may be surface treated with a plant-based phosphatide. Methods for this surface treatment have been taught in the art [33-35]. For example, a suitable phosphatide may be dissolved in a USP grade solvent such as USP heptane, sprayed onto the powder surface, dried, and subsequently heated at 100-150° C. to yield a permanently hydrophobic powder. The preferred range of phosphatide is 0.5-25% by weight and a more preferred level of phosphatide is 1.0-10% by weight. The preferred phosphatide is lecithin.

The zinc oxide may be surface treated by esterifying fatty alcohols or polyglyceryl (polyol) compounds to the particle surface. Methods for this surface treatment have been taught [36]. For example, a suitable fatty alcohol or polyglyceryl compound may be dissolved in a USP grade solvent such as USP isopropanol, sprayed onto the powder surface, dried, and subsequently heated at 130-200° C. to yield a permanently hydrophobic powder. The preferred range of fatty alcohol or polyglyceryl compound is 0.5-25% by weight and a more preferred level of fatty alcohol or polyglyceryl compound is 1.0-10% by weight. Suitable examples of fatty alcohols are stearyl alcohol, behenyl alcohol, octyldodecanol, and cetearyl alcohol. Suitable examples of polyglyceryl (polyol) compounds are polyglyceryl esters (for example, polyglyceryl-3 ricinoleate, polyglyceryl-6 ricinoleate, polyglyceryl-10 pentastearate and polyglyceryl-4 oleate), polyglyceryl polyesters (for example, polyglyceryl-4 diisostearate/polyhydroxystearate/sebacate, polyglyceryl-2 dipolyhydroxystearate and polyglyceryl-3 stearate/isostearate/dimer dilinoleate crosspolymer).

Preferably, the powder is hydrophobic. Hydrophobicity is measured using the following hydrophobicity test (this test is a visible water floatation test commonly used in the cosmetics industry, and is described in U.S. Pat. No. 4,454,288). Approximately 30 mL of deionized water is placed into a glass jar. Approximately 3.0 g±0.30 g of the powder to be tested is added into the glass jar. The glass jar is tightly sealed, and the sample is swirled around 4 to 5 times and vigorously shaken 4 to 5 times, so that intimate contact between the water and the powder is achieved. The powder is considered to be hydrophobic if the powder is buoyant (floating on the surface of the water) and water is clear after 15 minutes. The sample is marginally hydrophobic if the powder is not buoyant but the water is clear after 15 minutes, or if the powder is buoyant but the water is not clear after 15 minutes.

A dispersion of the zinc oxide powder in a liquid carrier may be prepared, either from the as prepared stoichiometric zinc oxide particle or following one or more surface treatments. The dispersion may be prepared by conventional formulation techniques. For example, the zinc oxide particles, an optional surfactant/dispersant and the liquid carrier may be combined in a vessel and stirred until homogenous. The dispersion may then be transferred to a mill, such as a media mill, and comminuted to achieve a desired average particle size.

The liquid carrier may be any fluid or wax that is lipophilic, preferably a cosmetically-acceptable fluid or wax, including mixtures thereof. Examples of suitable liquid carriers include triglycerides (for example, caprylic/capric triglycerides), esters (for example, C12-C15 alkyl benzoate, isopentyl laurate, isopropyl isostearate, coco-caprylate, coco-caprylate caprate, ethylhexyl isononanoate, tridecyl salicylate, ethylhexyl isononanoate, isodecyl salicylate, octyldodecyl neopentanoate, butyloctyl salicylate, jojoba esters and shea butter ethyl esters), natural oils and butters (for example, *Simmondsia chinensis* (jojoba) seed oil, shea butter, *Argania spinosa* (Argan) oil, pongami (karanja) oil and Limnanthes alba (white meadowfoam) seed oil), alkanes (for example, squalane, hemisqualane, isododecane and isohexadecane), silicones (for example, dimethicone, behenyl dimethicone, cetyl dimethicone, cetearyl methicone and phenyl dimethicone), waxes (for example, natural waxes, synthetic waxes and silicone waxes) and combinations thereof.

The surfactant/dispersant may be any surfactant or dispersant that has strong acid-base interactions with the raw or surface treated zinc oxide particles. Examples of suitable surfactants/dispersants include fatty alcohols and polyols (for example, stearyl alcohol, behenyl alcohol and cetearyl alcohol), fatty acids (for example, stearic acid and oleic acid), amino acids (for example, lauroyl lysine and myristoyl glutamate), polyglyceryl esters (for example, polyglyceryl-3 ricinoleate, polyglyceryl-6 ricinoleate, polyglyceryl-10 pentastearate and polyglyceryl-4 oleate), polyglyceryl polyesters (for example, polyglyceryl-4 diisostearate/polyhydroxystearate/sebacate, polyglyceryl-2 dipolyhydroxystearate and polyglyceryl-3 stearate/isostearate/dimer dilinoleate crosspolymer), polyesters with hydroxyl, amine or amide groups (for example, polyhydroxystearic acid), polyurethanes with hydroxyl, amine or amide groups, polyamides with hydroxyl, amine or amide groups, polyacrylates with hydroxyl, amine or amide groups, phosphate esters (for example, trilaureth-4 phosphate and triceteareth-4 phosphate), polymeric phosphoric acid salts (for example, 1,2-ethanediamine, polymers with aziridine, N-[3-[(2-ethylhexyl)oxy]-3-oxypropyl] derivatives and compounds including polyethylene-polypropylene glycol), phospholipids, ceramides, sphingosides (for example, lecithin, lysolecithin and ceramide 3), substituted silicones with groups (for example, cetyl diglyceryl tris(trimethylsiloxy)silylethyl dimethicone, CAS Number 104780-66-7 (Siloxanes and Silicones, di-Me, 3-hydroxypropyl group-terminated), CAS Number 102782-61-6 (Siloxanes and Silicones, di-Me, 3-hydroxypropyl Me) and CAS Number 106214-84-0 (Siloxanes and silicones, dimethyl, 3-aminopropyl)) and combinations thereof.

The zinc oxide particles may be present in the dispersion in an amount of 0.1-85.0% by weight, including 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 15.0%, 20.0%, 25.0%, 30.0%, 35.0%, 40.0%, 45.0%, 50.0%, 55.0%, 60.0%, 65.0%, 70.0%, 75%, 80%, and 85% by weight.

The surfactant/dispersant may be present in the dispersion in an amount of 1.0-100.0% of the mass of the zinc oxide particles, including 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 15.0%, 20.0%, 25.0%, 30.0%, 35.0%, 40.0%, 45.0%, 50.0%, 55.0%, 60.0%, 65.0%, 70.0%, 75.0%, 80.0%, 85.0%, 90.0% and 95.0%. Preferably, the surfactant is present in an amount of 2.0-60.0% of the mass of the zinc oxide particles.

The amount of liquid carrier in the dispersion will be dependent on the amount of the zinc oxide particles and the amount of the surfactant present in the dispersion. After combining the zinc oxide or surface treated zinc oxide particles and the surfactant, the carrier vehicle may be added in any suitable amount necessary to produce a desired dispersion.

The zinc oxide particles may be formed into the oil phase of a preparation or a powder preparation. Preferably, the preparation is suitable for topical application. Examples of suitable preparations include emulsions (oil-in-water and water-in-oil emulsions), sprays, balms, sticks, powders, powder-to-cream preparations, lipophilic preparations and anhydrous preparations.

Preparations containing the zinc oxide particles may be formulated for use in a variety of different applications. Examples of suitable formulations include cosmetics (for example, blushes, face powders, foundations, lipsticks, makeup bases and rouges), skin care products (for example, skin cleansing creams, lotions, liquids and pads; face and neck creams, lotions, powders and sprays; body and hand creams, lotions, powders and sprays; foot powders and sprays; moisturizers; night creams, lotions, powders and sprays; paste masks/mud packs; and skin fresheners) and sunscreens. Sunscreens are particularly preferred formulations. The formulations may be provided in any form suitable for topical administration, such as in the form of a topical suspension, lotion, cream, ointment, gel, hydrogel, foam, paste, tincture, liniment, sprayable liquid, aerosol, stick or powder. The formulations may optionally include inactive ingredients, auxiliaries and/or additives such as co-emulsifiers, fats, waxes, stabilizers, thickeners, biogenic active ingredients, film formers, fragrances, dyes, pearlizing agents, preservatives, pigments, electrolytes and pH regulators.

A sunscreen may include the zinc oxide particles and an additional UV radiation protectant. The UV radiation protectant may be any substance that absorbs, reflects and/or scatters UV radiation. The sunscreen may optionally include sun protection factor (SPF) boosters or stabilizers such as methoxycrylene and polyester-8. Examples of suitable additional UV radiation protectants include titanium dioxide ($TiO_2$), p-aminobenzoic acid (PABA), padimate O (OD-PABA, octyldimethyl-PABA, o-PABA), phenylbenzimidazole sulfonic acid (ensulizole, EUSOLEX® 232, PBSA, PARSOL® HS), cinoxate (2-ethoxyethyl p-methoxycinnamate), dioxybenzone (benzophenone-8), oxybenzone (benzophenone-3, EUSOLEX® 4360, ESCALOL® 567), homosalate (homomethyl salicylate, HMS), menthyl anthranilate (meradimate), octocrylene (EUSOLEX® OCR, 2-cyano-3,3-diphenyl acrylic acid, 2-ethylhexylester), octyl methoxycinnamate (octinoxate, EMC, OMC, ethylhexyl methoxycinnamate, ESCALOL® 557, 2-ethylhexyl-paramethoxycinnamate, PARSOL® MCX), octyl salicylate (octisalate, 2-ethylhexyl salicylate, ESCALOL® 587), sulisobenzone (2-hydroxy-4-methoxybenzophenone-5-sulfonic acid, 3-benzoyl-4-hydroxy-6-methoxybenzenesulfonic acid, benzophenone-4, ESCALOL® 577), trolamine salicylate (triethanolamine salicylate), avobenzone (1-(4-methoxyphenyl)-3-(4-tert-butylphenyl)propane-1,3-dione, butyl methoxy dibenzoylmethane, BMDBM, PARSOL® 1789, EUSOLEX® 9020), ecamsule (MEXORYL® SX, terephthalylidene dicamphor sulfonic acid), cerium oxide ($CeO_2$), drometrizole trisiloxane (MEXORYL® XL), bis-ethylhexyloxyphenol methoxyphenyl triazine (TINOSORB® S), bisoctrizole (TINOSORB® M, MILESTAB™ 360) and combinations thereof. Preferably, the additional UV radiation protectant has been approved by at least one of the regulatory agencies of the United States (U.S. Food and Drug Administration or FDA), Canada, the European Union, Australia, Japan, Korea, China, Mercosur, the Association of Southeast Asian Nations (ASEAN), the Commonwealth of Independent States (CIS) and the Gulf Cooperation Council (GCC).

A zinc oxide suitable for use in sunscreen applications must also meet the criterion of having a Critical Wavelength (see 76 FR 35660, Jun. 17, 2011, as amended at 76 FR 38975, Jul. 5, 2011) of at least 370 nm when in the fully dispersed state such as that described in the Color Test. If this criterion is not satisfied, products formulated from the zinc oxide will not meet the standard of providing broad spectrum protection in selected jurisdictions (see US 21CFR201.327 and Health Canada Sunburn Protectants Monograph of Oct. 12, 2006). The Critical Wavelength is identified as the wavelength at which the integral of the spectral absorbance curve reaches 90 percent of the integral over the UV spectrum from 290 nm to 400 nm. The equation below defines the Critical Wavelength:

$$\int_{290}^{\lambda_c} A(\lambda)d\lambda = 0.9 \int_{290}^{400} A(\lambda)d\lambda$$

Where $\lambda_c$=critical wavelength, $A(\lambda)$=mean absorbance at each wavelength, $d\lambda$=wavelength interval between measurements, A mean Critical Wavelength of 370 nm or greater is classified as broad spectrum protection. All the zinc oxides of non-comparative examples, below, have Critical Wavelength values ranging from 376 nm to 380 nm. Preferably, the stoichiometric zinc oxide has a Critical Wavelength value of at least 370 nm, more preferably at least 375 nm, including 376 to 380 nm. Preferably, the coated particles, the multilayer coated particles, dispersions, or cosmetic/dermatological compositions have a Critical Wavelength value of at least 370 nm, more preferably at least 375 nm, including 376 to 380 nm.

Formulations that include the zinc oxide particles provide a variety of health benefits due to the low propensity of generating photo-radicals upon UV exposure as evidenced by performance in the DPPH Photocatalytic Stability Test. It has been previously [32, 41, 42] demonstrated that zinc oxide particles that are characterized by low UV photoradical generation and are accordingly photocatalytically stable per the test previously described are able to (1) boost antioxidant performance in topical preparations exposed to UV radiation, (2) suppress free radical generation not only on the skin but also (3) in the dermal and epidermal layers of the skin following UV exposure based the results of electron spin resonance studies and (4) protect against the combined effects of UV radiation and environmental pollutants.

These properties allow the zinc oxide particles to treat or prevent oxidative stress or damage to the skin, hair and nails not only through the direct attenuation of UV radiation, but also through the suppression of free radicals and reactive oxygen species and thus protect keratinous material (such as the hair, fingernails, toenails and the outer layer of skin), protect human skin, suppress lipid peroxidation, prevent or reduce lines and wrinkles on the skin, prevent loss of elasticity of the skin, prevent thinning of the skin and prevent pigment darkening of the skin. These health benefits may be obtained by applying a formulation containing the zinc oxide particles to an area of skin, hair and/or nails.

One preferred aspect of the present invention includes the addition of antioxidants to dispersions containing the coated powders. Antioxidants are oxidized when exposed to UV radiation, leading to a decrease in the antioxidative power. Additionally, zinc oxide and other metal oxides are photoreactive, and produce free radicals upon UV radiation exposure. Metal oxides, in combination with antioxidants, would have a greater loss of AP than the antioxidants alone. However, by combining coated powders with antioxidants, the relative AP value of the dispersion remains higher than that of the antioxidants alone. Because the coated powders are super-photostable, compositions of coated powders and antioxidants exhibit a synergistic effect together. The antioxidants are able to be effective, because UV radiation is blocked or absorbed by the particles, preserving the AP value.

Dispersions may contain one or more antioxidant. Antioxidants may include vitamins, antioxidant minerals, antioxidant proteins, antioxidant enzymes and coenzymes, phytonutrients, antioxidant hormones, mycosporine-like amino acids (MAAs), antioxidants derived from marine algae, and other types of antioxidants. Antioxidants may be water soluble, fat soluble, or fat and water soluble. Suitable vitamins include vitamin A (including retinoids and carotenoids), vitamin C (ascorbic acid), vitamin E (tocopherols), and vitamin K. Suitable retinoids include retinol, retinoic acid (tretinoin), retinal and retinyl palmitate. Suitable minerals include copper, manganese, iodide and zinc. Suitable enzymes and coenzymes include melatonin, superoxide dismutase, catalase, and glutathione peroxidase. Suitable phytonutrients include carotenoids, flavonoids, phenolic acids, and nonflavonoid phenolics. Suitable carotenoids include alpha-carotene, retinal, astaxanthin, beta-carotene, canthaxanthin, lutein, lycopene, and zeaxanthin. Suitable flavonoids include hindered phenols, apigenin, luteolin, tangeritin, isohamnetin, kaempferol, myricetin, proanthocyanidins, quercetin, eriodictyol, hesperetin, naringenin, catechin, gallocatechin, epicatechin, epigallocatechin, thearubigins, daidzein, genistein, glycitein, resveratrol, pterostilbene, cyanidin, delphinidin, malvidin, pelargonidin, and petunidin. Suitable phenolic acids include phenol, polyphenols, alkylated phenols, and hindered phenols. Suitable phenols include butylated hydroxyanisole, butylated hydroxytluene, cannabinoids, capsaicin, carvacrol, cresol, estradiol, eugenol, gallic acid, guaiacol, thymol, tyrosine, and sesamol. Gallic acid includes salts and esters of gallic acid, also known as gallates. Suitable nonflavonoid phenolics include curcumin, flavonolignans, xanthones, and eugenol. Suitable mycosporine-like amino acids (MAAs) include mono-substituted MAAs, such as mycosporine-gycine and mycosporine-taurine, di-substituted MAAs, such as palythenic acid and shinorine, and derivatized MAAs, such as palythine-threonine sulfate and palythine-threonine glycoside. Examples of suitable MAAs can be found in Wada et al. (2015). Antioxidants derived from marine algae include ascorbate, glutathione, phlorotannins, eckol, eckstolonol, prenyl toluquinones, tetraprenyltoluquinols, sargothunbergol A, fucodiphlorethol, terpenoids, phycocyanin, phycocyanobilin, fucoxanthin, phlorotannin, and lutein. Other potential organic antioxidants include bilirubin, citric acid, oxalic acid, phytic acid, n-acetylcysteine, uric acid, green tea, hydoxy-tryrosol, dihydo-quercetin, ubiquinone, glutathione, alpha-lipoic acid, folic acid, ellagic acid, caffeic acid, and phytoestrogens. The antioxidants above also include any salt, ester or acid form of the antioxidant.

Dispersions may contain one or more phyto-extracts. A "phyto-extract" is a substance obtained from a plant. Preferably, the phyto-extract imparts a color. Phyto-extracts must be compatible with non-aqueous compositions; stable in air; non-staining to skin; non-irritating to skin in the amount used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color may no longer impart a color if they have been chemically modified. For example, curcumin imparts a yellow color but tetra-hydro curcumin, which has been hydrogenated, is colorless.

Dispersions may contain one or more plant bio-extracts. A "plant bio-extract" is a natural extract of a plant that provides a fragrance and may also provide a color. Plant bio-extracts must be compatible with non-aqueous compositions; stable in air; non-staining to skin; non-irritating to skin in the amounts used; and non-toxic in the amounts used. Synthetic versions of plant bio-extracts are outside the scope of the term "plant bio-extract." Examples of suitable plant bio-extracts include *arnica* extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis aspleniifolia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilla sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). All the above examples may include different species of the same genus of plant. For example, witch hazel extract may be obtained from *Hamamelis japonica, Hamamelis ovalis, Hamamelis mollis* or *Hamamelis virginiana*.

The composition optionally includes a phyto-extract. The phyto-extract may be selected to provide a color. Phyto-extracts that do not impart a color may also be included in the composition. Phyto-extracts must be compatible with non-aqueous compositions; stable in air; non-staining to skin; non-irritating to skin in the amounts used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color, such as curcumin, may no longer impart a color if they have been chemically modified, such as tetra-hydro curcumin. The composition may contain 0.01% to 5.0% phyto-extract, preferably 0.01% to 1.0% phyto-extract, including 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19% and 0.20% phyto-extract.

The composition optionally includes a plant bio-extract. The plant bio-extract provides a fragrance and may also provide a color. Plant bio-extracts must be compatible with non-aqueous compositions, such as being lipophilic or hydrophobic; stable in air; non-staining to skin; non-irritating to skin in the amounts used; and non-toxic in the amounts used. Examples of suitable plant bio-extracts include arnica extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis aspleniifolia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilla sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). The dispersion may optionally include extracts from algae species. These species include *Hijikia fusiformis, Spirulina platensis, Aphanizomenon, Spirulina maxima, Sargassum kjellamanianum, S. siliquastrum, Rhodomela confervoides, Symphjocladia latiuscula, Kappaphycus alvarezzi, Botiyococcus braunii, Dunallea salina, Cystoseira crinite, Ecklonia stolonifera, Sargassum thunbergii, S. thunbergii*, and *Ecklonia cava*. The composition may contain 0.10% to 10.0% plant bio-extract, preferably 2.0% to 6.0% plant bio-extract, including 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9% and 4.0% plant bio-extract.

The composition optionally includes an oil-soluble antioxidant. When an antioxidant is present, the antioxidant is different than the phyto-extract. Examples of suitable antioxidants include carotene, catechin, lycopene, resveratrol, Vitamin E or Vitamin A. "Vitamin E" may refer to any of the tocopherol or tocotrienol compounds that constitute the Vitamin E family of compounds, such as alpha-tocopherol and gamma-tocotrienol. The composition may contain 0.01% to 5.0% antioxidant, preferably 0.1% to 3.0% antioxidant, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% antioxidant.

The dispersion may contain one or more protist extract. A "protist extract" is a substance obtained from a protist. Protists include eukaryotic organisms that are not animals, plants or fungi. Preferably the protist extract is a substance that is high in astaxanthins. Examples of suitable protist extracts include plankton extract and algae extract, particularly red algae extract.

The dispersion may optionally include a protist extract. Preferably the protist extract is a substance that is high in astaxanthins. Examples of suitable protist extracts include plankton extract and algae extract, particularly red algae extract. The dispersion may contain 0.01% to 5.0% protist extract, preferably 0.1% to 3.0% protist extract, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% protist extract. Cosmetic and dermatological preparations may include cosmetic ingredients, auxiliaries and/or additives, for example, co-emulsifiers, fats and waxes, stabilizers, thickeners, biogenic active ingredients, film formers, fragrances, dyes, pearlizing agents, preservatives, pigments, electrolytes, and pH regulators. Suitable co-emulsifiers are, preferably, known W/O and also O/W emulsifiers, for example, polyglycerol esters, sorbitan esters or partially esterified glycerides. Typical examples of fats are glycerides; waxes such as beeswax, paraffin wax or microcrystalline waxes, optionally in combination with hydrophilic waxes. Stabilizers including metal salts of fatty acids, for example, magnesium, aluminum and/or zinc stearate. Examples of thickeners include crosslinked polyacrylic acids and derivatives thereof, polysaccharides, such as xanthan gum, guar gum, agar, alginates and tyloses, carboxymethylcellulose and hydroxyethylcellulose, and fatty alcohols, monoglycerides and fatty acids, polyacrylates, polyvinyl alcohol and polyvinylpyrrolidone. Biogenic active ingredients include plant extracts, protein hydrolyzates and vitamin complexes. Customary film formers include, for example, hydrocolloids, such as chitosan, microcrystalline chitosan or quaternary chitosan, polyvinylpyrrolidone, vinylpyrrolidone/vinyl acetate copolymers, polymers of the acrylic acid series, and quaternary cellulose derivatives. Examples of preservatives include parabens, diazolidinyl urea, iodopropynyl butylcarbamate, and sorbic acid. Examples of pearlizing agents include glycol distearic esters, such as ethylene glycol distearate, fatty acids and fatty acid monoglycol esters. Dyes which may be used are the substances suitable and approved for cosmetic purposes. Antioxidants, such as amino acids, retinol, flavonoids, polyphenols, vitamin C and tocopherols, may also be included.

The cosmetic and dermatological preparations may be in the form of a solution, dispersion or emulsions; for example, sunscreen preparations may be in liquid, paste or solid form, for example as water-in-oil creams, oil-in-water creams and lotions, aerosol foam creams, gels, oils, marking pencils, powders, sprays or alcohol-aqueous lotions. Solvents for these compositions include water; oils, such as triglycerides of capric acid or of caprylic acid, as well as castor oil; fats, waxes and other natural and synthetic fatty substances, esters of fatty acids with alcohols of low carbon number, for example with isopropanol, propylene glycol or glycerol, or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether. Other examples include isopropyl myristate, isopropyl palmitate, isopropyl stearate, isopropyl oleate, n-butyl stearate, diisopropyl adipate, n-hexyl laurate, n-decyl oleate, glyceryl stearate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and erucyl erucate.

The cosmetic and dermatological preparations may be in the form of solid sticks, and may include natural or synthetic waxes, fatty alcohols or fatty acid esters, liquid oils for example paraffin oils, castor oil, isopropyl myristate, semisolid constituents for example petroleum jelly, lanolin, solid constituents such as beeswax, ceresine and microcrystalline waxes and ozocerite, and high-melting waxes including carnauba wax and candelilla wax.

Cosmetic preparations may be in the form of gels and preferably include water, organic thickeners, for example gum arabic, xanthan gum, sodium alginate, cellulose derivatives such as methylcellulose, hydroxymethylcellulose, hydroxyethylcellulose, hydroxypropylcellulose, hydroxypropylmethylcellulose and inorganic thickeners, such as aluminum silicates, for example, bentonites, or a mixture of polyethylene glycol and polyethylene glycol stearate or distearate.

The zinc oxide and compositions containing the zinc oxide may be used in a method of protecting skin from light, including coating skin with a composition containing the zinc oxide particles. The zinc oxide and compositions containing the zinc oxide may be used in a method of protecting keratinous material including coating the keratinous material with a composition containing the zinc oxide particles. The zinc oxide and compositions containing the zinc oxide may be used in a method of protecting skin from light, including coating skin with a composition containing the zinc oxide particles. The zinc oxide and compositions containing the zinc oxide may be used in a method of suppressing lipid peroxidation including coating skin with a composition containing the zinc oxide particles. The zinc oxide and compositions containing the zinc oxide may be used in a method of preventing or reducing lines and wrinkles on the skin including coating skin with a composition containing the zinc oxide particles. The zinc oxide and compositions containing the zinc oxide may be used in a method of preventing loss of elasticity of the skin including coating skin with a composition containing the zinc oxide particles. The zinc oxide and compositions containing the zinc oxide may be used in a method of preventing thinning of the skin including coating skin with a composition containing the zinc oxide particles. The zinc oxide and compositions containing the zinc oxide may be used in a method of protecting skin from environmental pollution including coating skin with a composition containing the zinc oxide particles.

EXAMPLES

Example 1

Figure 2:
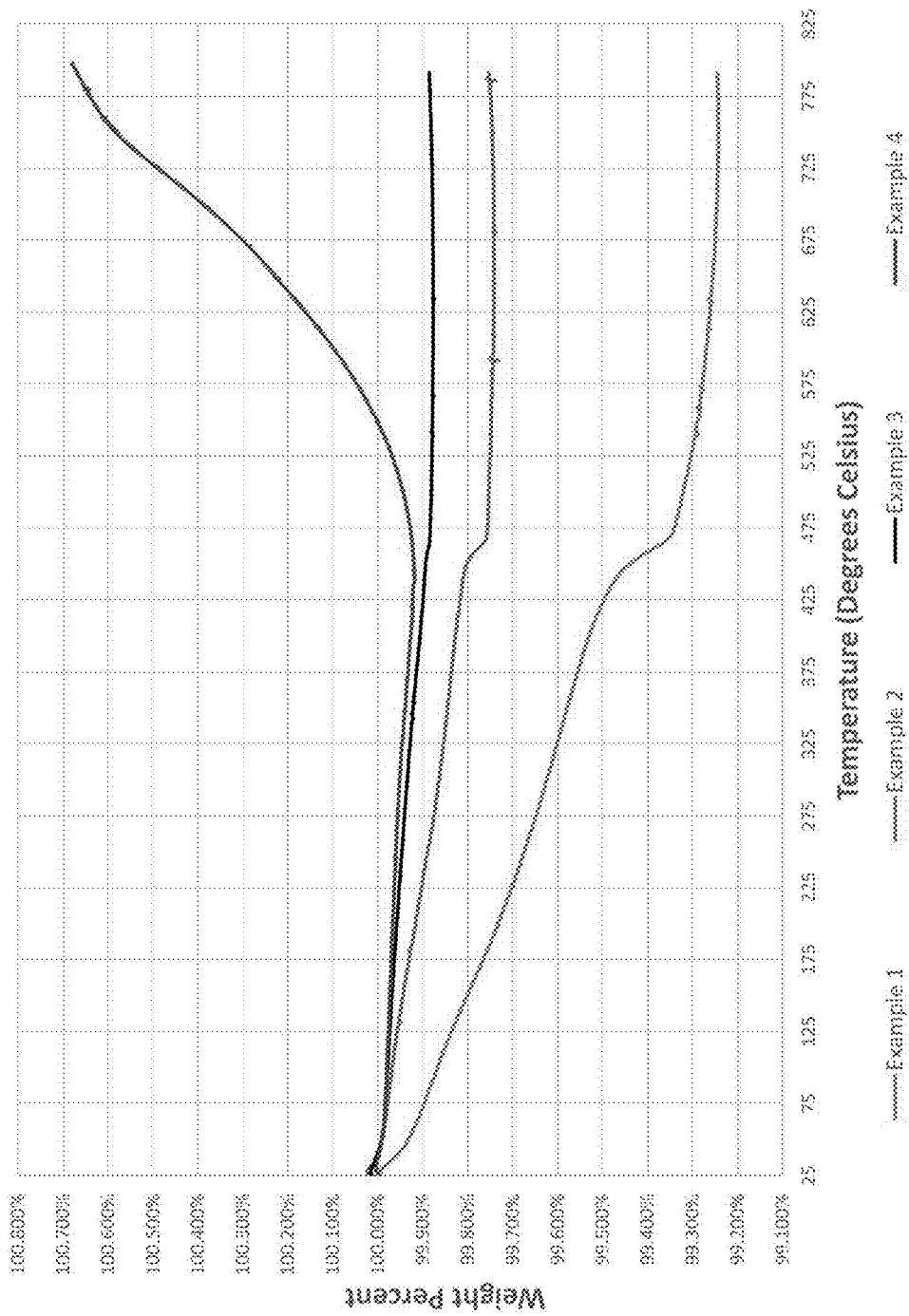
FIG. 2 is a graph showing the thermogravimetric analysis (TGA) of the zinc oxide powders of Examples 1-4.

USP grade zinc oxide particles having a hexagonal zincite crystal structure were produced via transferred arc physical vapor synthesis at a specific power input of 4.0 kW/kg ZnO and quench gas input of 5.3 ft$^3$ air/kg Zn vapor where the quench air is introduced at the closest point to the origin projected merged plasma jet that maintains a stable arc and utilizing an average transport air flow of 1300 ft$^3$ air/kg ZnO. The resulting powder product has an average particle size of 40 nm, a $\Delta E$ value of 17.69±0.26 (95% CI) in the Dispersion Color Test, a $\Delta E$ value of 7.22±0.29 in the DPPH Photocatalytic Stability Test, and $\Delta E$ value of 0.17±0.15 (95% CI) in the DPPH Dark Radical Test. Thermogravimetric analysis results, shown in FIG. 2, indicate the product to be stoichiometric ZnO.

Example 2: Comparative

USP grade zinc oxide particles having a hexagonal zincite crystal structure were produced via transferred arc physical vapor synthesis at a specific power input of 3.4 kW/kg ZnO and no quench gas input utilizing an average transport air flow of 1,130 ft$^3$ air/kg ZnO. The resulting white powder product has an average particle size of 150 nm, a $\Delta E$ value of 9.51±0.10 (95% CI) in the Dispersion Color Test and a $\Delta E$ value of 18.57±0.17 in the DPPH Photocatalytic Stability Test. Thermogravimetric analysis results, shown in FIG. 2, indicate the product to be stoichiometric ZnO.

Example 3: Comparative Stoichiometric Zinc Oxide Reference

The powder of Example 2 was calcined in air at 800° C. for 1 hour. The resulting white powder product has an average particle size of 300 nm, a $\Delta E$ value of 9.69 in the Dispersion Color Test and a $\Delta E$ value of 34.80 in the DPPH Photocatalytic Stability Test. Thermogravimetric analysis results, shown in FIG. 2, confirm the product to be stoichiometric ZnO.

Example 4: Comparative U.S. Pat. No. 6,869,956

The powder of Example 3 was reduced in a hydrogen/nitrogen atmosphere. The resulting powder product displayed a green luminescence when irradiated with UVA radiation, has a $\Delta E$ value of 16.50 in the Dispersion Color Test and a $\Delta E$ value of 16.45 in the DPPH Photocatalytic Stability Test. The results of the DPPH Photocatalytic Stability Test are consistent with that of comparative compositions since the $\Delta E$ value is less than that of the parent zinc oxide and is statistically significant. The results also clearly indicate that the material is not photocatalytically stable when compared to the stoichiometric zinc oxide and are, in fact, found to be less photocatalytically stable than some commercial zinc oxides that do not display noticeable coloration (see Example 15). The composition of this example also produced a ΔE value of 10.21 in the DPPH Dark Radical Test (see below), indicating that the composition produces free radicals in the dark, suggesting that this material is not ideal for topical UV protective formula environments. This is in sharp contrast to the stoichiometric zinc oxide. Thermogravimetric analysis results, shown in FIG. 2, indicate the product to be sub-stoichiometric ZnO based on the distinct mass gain feature with an onset at about 450 C°. The TGA analysis may be used to calculate the composition which is approximately $ZnO_{0.96}$ and is thus significantly deficient in oxygen, in sharp contrast with the stoichiometric zinc oxide.

Free radical generation of a zinc oxide powder in the absence of exposure to radiation is measured using the test described below. This test is referred to as the "DPPH Dark Radical Test." First, 0.025 g±0.001 g of ZnO powder on an actives basis is added to six 50 mL disposable plastic beakers. 0.0125% DPPH (di(phenyl)-(2,4,6-trinitrophenyl) iminoazanium, also referred to as diphenylpicrylhydrazyl; CAS Number 1898-66-4) is prepared in BCS (ethylene glycol butyl ether). 19.950 g±0.001 of 0.0125% DPPH in BCS solution and 0.025 g±0.001 g of deionized water are added to each beaker containing zinc oxide powder. In the case of zinc oxide actives being tested from a dispersion, 0.025 g±0.001 of zinc oxide actives are added from a dispersion of known zinc oxide content to six 50 mL disposable plastic beakers. A nominal 0.0125% DPPH solution is prepared in BCS (ethylene glycol butyl ether) where the concentration of BCS is adjusted in a quantity sufficient manner to compensate for the liquid dispersion carrier and any other excipient ingredients in the zinc oxide containing dispersion. 19.975 g±0.001 of the adjusted nominal 0.0125% DPPH in BCS solution and 0.025 g±0.001 g of deionized water are added to each beaker containing zinc oxide dispersion. Samples are mixed thoroughly with a glass stir rod, and each beaker is sonicated for 60 seconds, ensuring the particles are well-dispersed throughout the solution. After sonication, the sample is transferred to a labelled scintillation vial. The samples are next transferred to a dark chamber maintained at 40±2° C. for exactly 60 minutes. Following the one-hour dark hold period, each sample is transferred to centrifuge tubes and centrifuged at 5000 RCF for 15 minutes followed by filtration using a 0.2 micron PVDF syringe filter to remove all particulate material. For each sample, 10 ml of this filtered solution is transferred into a new scintillation vial for color testing. A Color Reference is prepared adding 19.950 g±0.001 of 0.0125% DPPH in BCS solution and 0.025 g±0.001 g of deionized water to a scintillation vial followed by thorough mixing. 10 ml of this reference solution is transferred into a new scintillation vial which serves as a Color Reference for color testing.

The color of each sample and the Color Reference is measured on a Konica Minolta colorimeter CM-600D Colorimeter or suitable equivalent colorimeter calibrated using a NIST traceable white tile. This test is referred to as the "Dispersion Color Test". Color difference may be expressed as the total color change relative to the Color Reference (ΔE in L*a*b* color space). ΔE is calculated from the following expression, as per the CIE76 definition:

$$\Delta E = \sqrt{(L_2^* - L_1^*)^2 + (a_2^* - a_1^*)^2 + (b_2^* - b_1^*)^2}$$

where $L_2^*$, $a_2^*$, and $b_2^*$ are the color coordinates of test samples and where $L_1^*$, $a_1^*$, and $b_1^*$ are the color coordinates of Color Reference. Data is reported as the average ΔE value of the six samples. A particle with no propensity for free radical generation in the dark should yield a solution which has no perceptible color difference from that of the Color Reference. Quantitatively, a particle is considered to generate free radicals in the absence of irradiation if ΔE>1.0 in the above DPPH dark radical test.

Example 5

The powder of Example 1 was surface treated with 2% lecithin on powder mass and dispersed in caprylic/capric triglyceride carrier at 72 weight % zinc oxide using 8% polyglyceryl-2 dipolyhydroxystearate on powder mass as a dispersant. The powder was wetted into dispersion using a propeller blade mixer and dispersed using low intensity ultrasonication. The resulting dispersion was pourable and had a deep characteristic orange to tan color. The resulting dispersion product has a ΔE value of 17.98 in the Dispersion Color Test and a ΔE value of 7.12 in the DPPH Photocatalytic Stability Test.

Example 6

The powder of Example 1 was surface treated with 2% lecithin on powder mass and dispersed in coco-caprylate caprate carrier at 75 weight % zinc oxide using 6% polyglyceryl-2 dipolyhydroxystearate on powder mass as a dispersant. The powder was wetted into dispersion using a propeller blade mixer and transferred to a horizontal media mill for milling. The dispersion was milled using 0.3 mm yttria stabilized zirconia media until the dispersion product produced a ΔE value of 17.64 in the Dispersion Color Test (milling time was 330 minutes). The resulting product is pourable and has a ΔE value of 7.04 in the DPPH Photocatalytic Stability Test.

Example 7

The powder of Example 1 was surface treated with 2% lecithin on powder mass and dispersed in coco-caprylate caprate carrier at 75 weight % zinc oxide using 6% polyglyceryl-2 dipolyhydroxystearate on powder mass as a dispersant. The powder was wetted into dispersion using a propeller blade mixer and transferred to a horizontal media mill for milling. The dispersion was milled using 0.2 mm yttria stabilized zirconia media until the dispersion product produced a ΔE value of 19.74 in the Dispersion Color Test (milling time was 450 minutes). The resulting product has a ΔE value of 6.53 in the DPPH Photocatalytic Stability Test.

Example 8

The dispersion of Example 7 was returned to the horizontal media mill for milling. The dispersion was further milled using 0.2 mm yttria stabilized zirconia media until the dispersion product produced a ΔE value of 25.04 in the Dispersion Color Test (milling time was 870 minutes). The resulting product has a ΔE value of 4.70 in the DPPH Photocatalytic Stability Test.

Example 9

The powder of Example 3 was dispersed in coco-caprylate caprate carrier at 30 weight % zinc oxide using 3% polyglyceryl-2 dipolyhydroxystearate and 1% lecithin on powder mass as dispersants. The dispersion was transferred to a horizontal media mill for milling. The dispersion was milled using 0.3 mm yttria stabilized zirconia media until the dispersion product produced a ΔE value of 20.51 in the Dispersion Color Test (milling time was 80 minutes). The resulting product has a ΔE value of 9.65 in the DPPH Photocatalytic Stability Test.

Example 10

The dispersion of Example 9 was returned to the horizontal media mill for further milling. The dispersion was milled using 0.3 mm yttria stabilized zirconia media until the dispersion product produced a ΔE value of 25.45 in the Dispersion Color Test (milling time was 120 minutes). The resulting product has a ΔE value of 6.92 in the DPPH Photocatalytic Stability Test. Thermogravimetric analysis showed no mass gain features above 400° C. and a small mass loss of 0.36% between 400° C. and 800° C. indicating the product remained as stoichiometric ZnO.

Example 11

The powder of Example 2 was subjected to a silanizing surface treatment using 2.5% by weight of octyltriethoxysilane on powder mass. The resultant powder was dispersed in caprylic/capric triglyceride carrier at 70 weight % zinc oxide using 2.5% by weight polyhydroxystearic acid on powder mass. The powder was wetted into dispersion using a propeller blade mixer. Initially the dispersion displayed a white color. The dispersion was transferred to a horizontal media mill and milled using 0.3 mm yttria stabilized zirconia media until the dispersion product produced a ΔE value of 17.15 in the Dispersion Color Test (milling time was 120 minutes). The resulting product has a ΔE value of 9.02 in the DPPH Photocatalytic Stability Test. This ΔE represents only 49% of the ΔE value of the starting powder from Example 2.

Example 12

The powder of Example 2 was subjected to a surface treatment comprising propylsilsesquioxane/dimethiconol/silicate crosspolymer where the resultant powder is 92% zinc oxide by weight. This powder was dispersed in squalane at 64 weight % zinc oxide using 10% by weight lecithin on powder mass. Initially the dispersion displayed a white color. The dispersion was transferred to a horizontal media mill and milled using 0.3 mm yttria stabilized zirconia media until the dispersion product produced a ΔE value of 19.16 in the Dispersion Color Test (milling time was 60 minutes). The resulting product has a ΔE value of 4.02 in the DPPH Photocatalytic Stability Test.

Example 13

The powder of Example 1 was surface treated with silica to yield a powder comprising 92% zinc oxide by weight. The resultant powder was dispersed in caprylic/capric triglyceride carrier at 60.3 weight % zinc oxide using 2% lecithin and 6% polyglyceryl-2 dipolyhydroxystearate on powder mass as dispersants. The powder was wetted into dispersion using a propeller blade mixer and the resultant dispersion displayed an initial tan color. The dispersion was transferred to a horizontal media mill for milling. The dispersion was milled using 0.2 mm yttria stabilized zirconia media until the dispersion product resulted in a ΔE value of 17.08 in the Dispersion Color Test (milling time was 180 minutes). The resulting product has a ΔE value of 1.68 in the DPPH Photocatalytic Stability Test.

Example 14

The powder of Example 2 was surface treated with silica to yield a powder comprising 96% zinc oxide by weight. The resultant powder was dispersed in squalane carrier at 60.5 weight % zinc oxide using 2.5% lecithin as a dispersant. Initially the dispersion displayed a white color. The dispersion was transferred to a horizontal media mill and milled using 0.3 mm yttria stabilized zirconia media until the dispersion product produced a ΔE value of 19.44 in the Dispersion Color Test (milling time was 180 minutes). The resulting product has a ΔE value of 2.97 in the DPPH Photocatalytic Stability Test.

Example 15: Comparative Commercial Zinc Oxides

Ten (10) commercial zinc oxide UV filters were sourced globally for evaluation by the Dispersion Color Test and DPPH Photocatalytic Stability Test. Materials were obtained from each global region where zinc oxide UV filters are manufactured at scale. Product formats representing both powders and dispersions were evaluated. The materials are denoted as "Example 15 Commercial Material 1-10". The results of the tests are presented in Table 1 together with the results of the previous samples. All the commercial materials had ΔE values of less than 12 in the Dispersion Color Test and ΔE values greater than 15 in the DPPH Photocatalytic Stability Test indicating that they are not photocatalytically stable.

Figure 3:
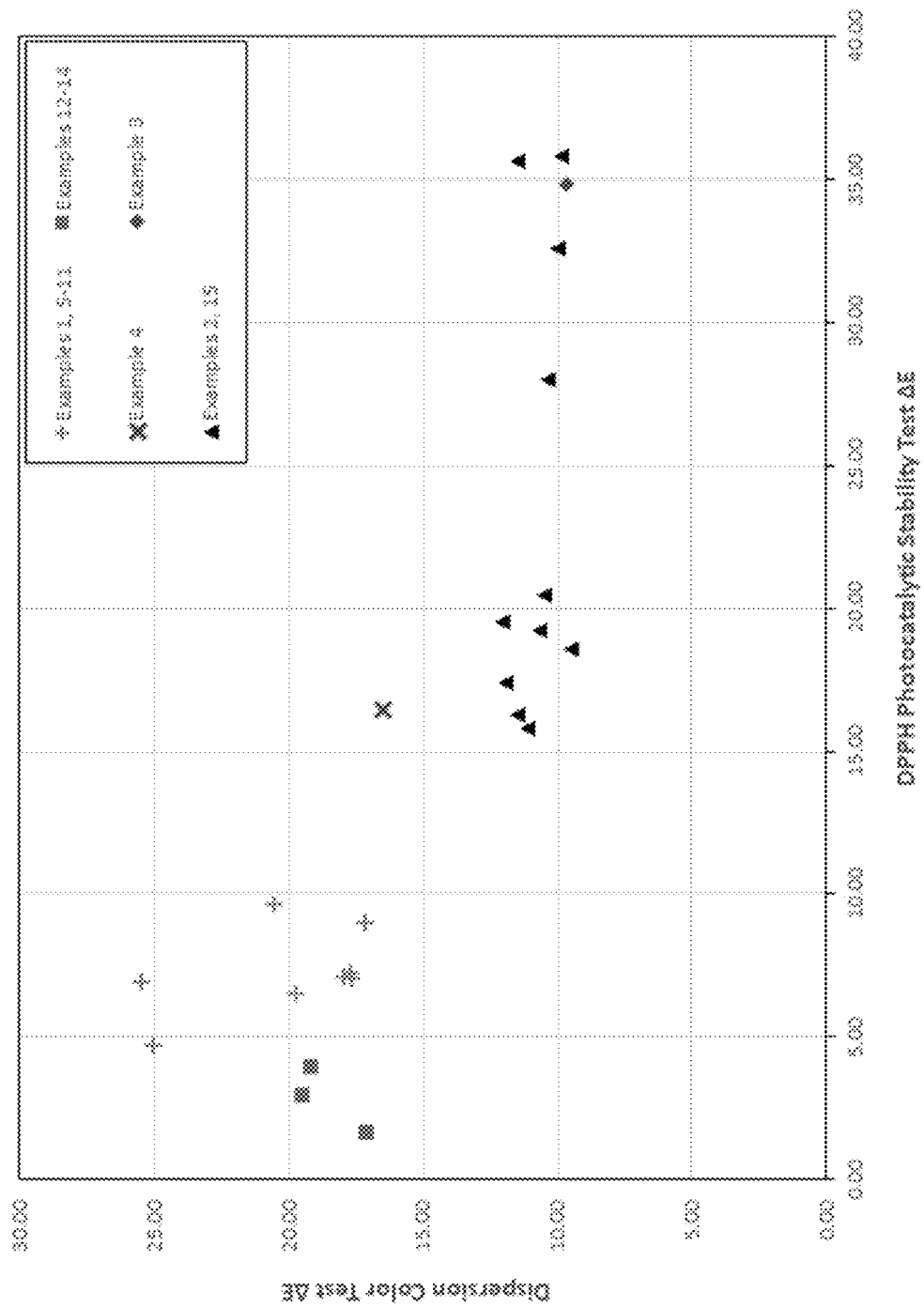
FIG. 3 is graph of the results of the DPPH Photocatalytic Stability Test (horizontal axis) versus the results of the Dispersion Color Test (vertical axis) for the zinc oxides powders of Examples 1-15.

The Dispersion Color Test ΔE values are plotted against the DPPH Photocatalytic Stability ΔE values for all materials described in Examples 1-15 and presented in FIG. 3. It is apparent from the data that the inventive compositions display distinct characteristics compared to comparative compositions. Note that the data pertaining to the stoichiometric zinc oxides that have been surface treated to even further enhance their inherent photocatalytic stability (Examples 12-14) are denoted in the figure by different symbols than those stoichiometric zinc oxides whose DPPH Photocatalytic Stability ΔE values reflect the property of the stoichiometric zinc oxide particles without coatings or in which the coating does not significantly affect the photocatalytic stability.

TABLE 1

| Material | Dispersion Color Test ΔE | Photocatalytic stability DPPH Test ΔE |
|---|---|---|
| Example 1 | 17.69 | 7.22 |
| Example 2 | 9.51 | 18.57 |
| Example 3 | 9.69 | 34.80 |
| Example 4 | 16.50 | 16.45 |
| Example 5 | 17.98 | 7.12 |
| Example 6 | 17.64 | 7.04 |
| Example 7 | 19.74 | 6.53 |
| Example 8 | 19.16 | 4.02 |
| Example 9 | 20.51 | 9.65 |
| Example 10 | 25.45 | 6.92 |
| Example 11 | 17.15 | 9.02 |
| Example 12 | 19.16 | 4.02 |
| Example 13 | 17.08 | 1.68 |
| Example 14 | 19.44 | 2.97 |
| Example 15 Commercial Material 1 | 11.48 | 16.24 |

TABLE 1-continued

| Material | Dispersion Color Test ΔE | Photocatalytic stability DPPH Test ΔE |
|---|---|---|
| Example 15 Commercial Material 2 | 9.87 | 35.82 |
| Example 15 Commercial Material 3 | 10.48 | 20.47 |
| Example 15 Commercial Material 4 | 10.37 | 27.97 |
| Example 15 Commercial Material 5 | 12.02 | 19.52 |
| Example 15 Commercial Material 6 | 11.91 | 17.39 |
| Example 15 Commercial Material 7 | 9.97 | 32.60 |
| Example 15 Commercial Material 8 | 11.49 | 35.64 |
| Example 15 Commercial Material 9 | 11.09 | 15.83 |
| Example 15 Commercial Material 10 | 10.64 | 19.23 |

Example 16

The powder of Example 1 was surface treated with lecithin at 8% by weight on zinc oxide powder. Lecithin was first dissolved in USP heptane at 40% by weight and the solution was sprayed onto the powder under mixing in an inert environment in an amount sufficient to yield the final target composition. The resultant mixture was dried and heat treated in air at 110° C. The resulting powder product passes the Hydrophobicity Test.

Example 17

The powder of Example 1 was surface treated with cetearyl alcohol at 5% by weight on zinc oxide powder. Cetearyl alcohol was first dissolved in USP isopropanol at 20% by weight and the solution was sprayed onto the powder under mixing in an inert environment in an amount sufficient to yield the final target composition. The resultant mixture was dried and heat treated in air at 130° C. to yield an esterified surface treatment. The resulting powder product passes the Hydrophobicity Test.

Example 18

The powder of Example 1 was surface treated with octyldodecanol at 8% by weight on zinc oxide powder. Octyldodecanol was first mixed with in USP isopropanol at 40% by weight and the solution was sprayed onto the powder under mixing in an inert environment in an amount sufficient to yield the final target composition. The resultant mixture was dried and heat treated in air at 130° C. to yield an esterified surface treatment. The resulting powder product passes the Hydrophobicity Test.

Example 19

The silica surface treated powder of Example 13 was further surface treated with lecithin at 8% by weight on powder. Lecithin was first dissolved in USP heptane at 40% by weight and the solution was sprayed onto the powder under mixing in an inert environment in an amount sufficient to yield the final target composition. The resultant mixture was dried and heat treated in air at 110° C. The resulting powder product passes the Hydrophobicity Test.

Example 20

The silica surface treated powder of Example 13 was further surface treated with cetearyl alcohol at 5% by weight on powder. Cetearyl alcohol was first dissolved in USP isopropanol at 20% by weight and the solution was sprayed onto the powder under mixing in an inert environment in an amount sufficient to yield the final target composition. The resultant mixture was dried and heat treated in air at 130° C. to yield an esterified surface treatment. The resulting powder product passes the Hydrophobicity Test.

Example 21

The silica surface treated powder of Example 13 was further surface treated with octyldodecanol at 8% by weight on powder. Octyldodecanol was first mixed with in USP isopropanol at 40% by weight and the solution was sprayed onto the powder under mixing in an inert environment in an amount sufficient to yield the final target composition. The resultant mixture was dried and heat treated in air at 130° C. to yield an esterified surface treatment. The resulting powder product passes the Hydrophobicity Test.

Example 22

This Example demonstrates a water-in-oil emulsion cosmetic sunscreen preparation.

The ingredients in their respective phases are listed below:

TABLE 2

Sunscreen Emulsion Ingredients

| | Ingredients | Parts by Weight |
|---|---|---|
| Phase A | Water USP | 52.25 |
| | Glycerin USP | 2.00 |
| | Sodium Chloride USP | 0.70 |
| | Magnesium Sulfate USP | 0.15 |
| | Caprylyl Glycol and Ethylhexylglcerin and Hexylene Glycol and Phenoxyethanol | 1.00 |
| Phase B | Caprylyl Caprylate/Caprate | 7.00 |
| | Dispersion of Example 7 | 16.00 |
| | Squalane | 4.94 |
| | C12-15 Alkyl Benzoate | 9.46 |
| | Polyglyceryl-2 Dipolyhydroxystearate | 3.75 |
| | Polyglyceryl-3 Diisostearate | 2.75 |
| | Total | 100.00 |

The formulation is prepared by first combining the ingredients of Phase A in a heated vessel and heated to 80° C. while mixing until uniform. Next, the ingredients of Phase B are combined in a heated vessel and heated to 80° C. while mixing until uniform. Phase A is then added to Phase B while homogenizing using a rotor-stator type homogenizer for 5 minutes at 5000 RPM until uniform. The formula is then cooled to 25° C. while continuously mixed at low speed.

Example 23

This Example demonstrates a water-in-oil emulsion cosmetic sunscreen preparation. The ingredients in their respective phases are listed below:

TABLE 3

Sunscreen Emulsion Ingredients

| | Ingredients | Parts by Weight |
|---|---|---|
| Phase A | Water USP | 52.25 |
| | Glycerin USP | 2.00 |
| | Sodium Chloride USP | 0.70 |

TABLE 3-continued

Sunscreen Emulsion Ingredients

| | Ingredients | Parts by Weight |
|---|---|---|
| | Magnesium Sulfate USP | 0.15 |
| | Caprylyl Glycol and Ethylhexylglcerin and Hexylene Glycol and Phenoxyethanol | 1.00 |
| Phase B | Caprylyl Caprylate/Caprate | 7.00 |
| | Dispersion of Example 13 | 19.90 |
| | Squalane | 4.94 |
| | C12-15 Alkyl Benzoate | 5.56 |
| | Polyglyceryl-2 Dipolyhydroxystearate | 3.75 |
| | Polyglyceryl-3 Diisostearate | 2.75 |
| | Total | 100.00 |

The formulation is prepared by first combining the ingredients of Phase A in a heated vessel and heated to 80° C. while mixing until uniform. Next, the ingredients of Phase B are combined in a heated vessel and heated to 80° C. while mixing until uniform. Phase A is then added to Phase B while homogenizing using a rotor-stator type homogenizer for 5 minutes at 5000 RPM until uniform. The formula is then cooled to 25° C. while continuously mixed at low speed.

Example 24: (Prophetic)

A concealer stick composition providing UV protection is prepared as an anhydrous formula comprising the stoichiometric zinc oxide. The composition is given in the Table below.

TABLE 4

Sunscreen Concealer Stick Ingredients

| Ingredients | Parts by Weight |
|---|---|
| Phase A | |
| Coco Caprylate | 4.60 |
| Propylheptyl Caprylate | 17.00 |
| Dispersion of Example 7 | 20.00 |
| Titanium Dioxide, Disodium Stearoyl Glutamate, Aluminum Hydroxide | 7.00 |
| Iron Oxides, Disodium Stearoyl, Glutamate, Aluminum Hydroxide | 0.10 |
| Iron Oxides, Disodium Stearoyl, Glutamate, Aluminum Hydroxide | 0.70 |
| Iron Oxides, Disodium Stearoyl, Glutamate, Aluminum Hydroxide | 0.30 |
| Phase B | |
| Cetearyl Alcohol | 5.00 |
| Hydrogenated Castor Oil | 6.00 |
| Pentaerythrityl Distearate | 4.00 |
| Polyglyceryl-2 Dipolyhydroxystearate | 1.00 |
| Phase C | |
| Talc | 29.80 |
| Aluminum Starch Ocetnylsuccinate | 3.00 |
| Phase D | |
| Preservative | 1.00 |
| Phase E | |
| Fragrance | 0.50 |
| Total | 100.00 |

The formulation is processed as follows. Phase A is combined and mixed under high shear conditions. Phase B is added to Phase A and the mixture is heated to 85° C. under high shear conditions. Phase C is dispersed into the mixture under high shear conditions while maintaining the temperature at 85° C. The batch is then cooled under high shear mixing. Once below 65° C., Phases D and E are added to the mixture step-wise under high shear mixing conditions. The batch is allowed to continue cooling and dispensed into final packaging once the temperature reaches 60° C.

Example 25: (Prophetic)

A concealer stick composition providing UV protection is prepared as an anhydrous formula comprising the stoichiometric zinc oxide. The composition is given in the Table below.

TABLE 5

Sunscreen Concealer Stick Ingredients

| Ingredients | Parts by Weight |
|---|---|
| Phase A | |
| Coco Caprylate | 1.40 |
| Propylheptyl Caprylate | 17.00 |
| Dispersion of Example 13 | 23.20 |
| Titanium Dioxide, Disodium Stearoyl Glutamate, Aluminum Hydroxide | 7.00 |
| Iron Oxides, Disodium Stearoyl, Glutamate, Aluminum Hydroxide | 0.10 |
| Iron Oxides, Disodium Stearoyl, Glutamate, Aluminum Hydroxide | 0.70 |
| Iron Oxides, Disodium Stearoyl, Glutamate, Aluminum Hydroxide | 0.30 |
| Phase B | |
| Cetearyl Alcohol | 5.00 |
| Hydrogenated Castor Oil | 6.00 |
| Pentaerythrityl Distearate | 4.00 |
| Polyglyceryl-2 Dipolyhydroxystearate | 1.00 |
| Phase C | |
| Talc | 29.80 |
| Aluminum Starch Ocetnylsuccinate | 3.00 |
| Phase D | |
| Preservative | 1.00 |
| Phase E | |
| Fragrance | 0.50 |
| Total | 100.00 |

The formulation is processed as follows. Phase A is combined and mixed under high shear conditions. Phase B is added to Phase A and the mixture is heated to 85° C. under high shear conditions. Phase C is dispersed into the mixture under high shear conditions while maintaining the temperature at 85° C. The batch is then cooled under high shear mixing. Once below 65° C., Phases D and E are added to the mixture step-wise under high shear mixing conditions. The batch is allowed to continue cooling and dispensed into final packaging once the temperature reaches 60° C.

Example 26: (Prophetic)

A cosmetic dry powder sunscreen formulation is prepared comprising the stoichiometric zinc oxide. The composition is given in the Table below.

TABLE 6

| Dry Powder Sunscreen Ingredients | |
| --- | --- |
| Ingredients | Parts by Weight |
| Mica and Methicone | 34.00 |
| Silica silylate | 31.00 |
| Powder of Example 18 | 26.00 |
| Iron oxides and Triethoxycaprylylsilane | 8.00 |
| Preservative | 1.00 |
| Total | 100.00 |

The dry powder ingredients are blended and milled until uniform.

Example 27: (Prophetic)

A cosmetic dry powder sunscreen formulation is prepared comprising the stoichiometric zinc oxide. The composition is given in the Table below.

TABLE 7

| Dry Powder Sunscreen Ingredients | |
| --- | --- |
| Ingredients | Parts by Weight |
| Mica and Methicone | 34.00 |
| Silica silylate | 28.70 |
| Powder of Example 18 | 28.30 |
| Iron oxides and Triethoxycaprylylsilane | 8.00 |
| Preservative | 1.00 |
| Total | 100.00 |

The dry powder ingredients are blended and milled until uniform.

REFERENCES

1. H. Rafla-Yuan and J. F Cordaro, *J. Applied Phys.* 74, 4685 (1993).
2. J. C. Simpson and J. F Cordaro, *J. Applied Phys.* 63, 1781 (1988).
3. M. D. McCluskey and S. J. Jokela, *J. Applied Phys.* 106, 071101 (2009).
4. L. Schmidt-Mende and J. L. Macmanus-Driscoll, *Materials Today*, 10 (5), 40 (2007).
5. U.S. Pat. No. 5,223,250
6. U.S. Pat. No. 5,441,726
7. U.S. Pat. No. 5,536,492
8. U.S. Pat. No. 6,869,596
9. G. Yi, G. Agarwal, and Y. Zhang, *J. Phys. Chem. C* 123, 19230 (2019).
10. U.S. Pat. No. 2,616,842
11. U.S. Pat. No. 3,900,762
12. U.S. Pat. No. 4,642,207
13. U.S. Pat. No. 4,732,369
14. U.S. Pat. No. 5,460,701
15. U.S. Pat. No. 5,874,684
16. U.S. Pat. No. 7,517,513
17. C. F. Bohren, D. Huffman, Absorption and scattering of light by small particles (John Wiley, New York 1983).
18. U.S. Pat. No. 2,885,366
19. U.S. Pat. No. 3,437,502
20. U.S. Pat. No. 4,845,054
21. U.S. Pat. No. 2,938,009
22. U.S. Pat. No. 6,214,106
23. U.S. Pat. No. 3,849,152
24. U.S. Pat. No. 3,920,865
25. U.S. Pat. No. 5,486,631
26. U.S. Pat. No. 5,565,591
27. U.S. Pat. No. 5,756,788
28. U.S. Pat. No. 5,993,967
29. U.S. Pat. No. 6,033,781
30. U.S. Pat. No. 9,139,737
31. US Pat. Publication 20180291210A1
32. U.S. Pat. No. 10,555,892
33. U.S. Pat. No. 4,056,494
34. U.S. Pat. No. 4,126,591
35. U.S. Pat. No. 4,305,853
36. U.S. Pat. No. 2,657,149
37. (not used in text)
38. A. J. Cox, Alan J. DeWeerd, and J. Linden, *Am. J. Phys,* 70, 620 (2002)
39. R. Gers, E. Climent, D. Legendre, D. Anne-Archard, and C. Frances, *Chemical Engineering Science,* 65, 2052 (2010).
40. R. J Tamblyn, Ph.D. Dissertation, University of Birmingham (2009).
41. H. W. Sarkas, K. Cureton, and K. Jung, *Eurocosmetics,* 5, 20 (2018).
42. E. F. Bernstein, W. W. Sarkas, and P. Boland, *J. Cosmet. Dermatol.,* 00, 1-9 (2019).
43. Federal Register 63 FR 56584.
44. 21CRF352.10 (Sunscreen Drug Products for Over-The-Counter Human Use).
45. Federal Register 84 FR 6204.
46. U.S. Pat. No. 10,183,868.

What is claimed is:

1. Zinc oxide particles, wherein the particles have:
   an O:Zn ratio of at least 0.99,
   an average particle size of 10 to 300 nm,
   a sufficient concentration of oxygen vacancies and zinc vacancies to give a dispersion of the particles in C12-C15 alkyl benzoate an orange to tan color corresponding to a ΔE value of at least 15 in a Dispersion Color Test;
   wherein the ΔE in the Dispersion Color Test is calculated as:

$$\Delta E = \sqrt{(L_2^* - L_1^*)^2 + (a_2^* - a_1^*)^2 + (b_2^* - b_1^*)^2},$$

wherein $L_2^*$, $a_2^*$, and $b_2^*$ are the color coordinates of a zinc oxide particle test sample and wherein $L_1^* = 99.47$, $a_1^* = -0.16$, and $b_1^* = -0.17$ correspond to color coordinates of a white reference tile; and
   wherein the particles contain no aggregates and have no detectable particles 500 nm or larger, on a number-weighted basis.

2. The zinc oxide particles of claim 1, wherein the particles are photocatalytically stable.

3. The zinc oxide particles of claim 1, wherein the particles have an average particle size of 15 to 200 nm.

4. The zinc oxide particles of claim 1, wherein the particles have a ΔE value of 1 to 10 in a diphenylpicrylhydrazyl (DPPH) Photocatalytic Stability Test;
   wherein the ΔE value in the DPPH Photocatalytic Stability Test is calculated as:

$$\Delta E = \sqrt{(L_2^* - L_1^*)^2 + (a_2^* - a_1^*)^2 + (b_2^* - b_1^*)^2},$$

wherein $L_2^*$, $a_2^*$ and $b_2^*$ are the color coordinates of a zinc oxide particle test mixture post irradiation and where $L_1^*$, $a_1^*$, and $b_1^*$ are the initial color coordinates of the zinc oxide particle test mixture prior to irradiation.

5. The zinc oxide of claim 1, wherein the particles have a ΔE value of 15 to 26 in the Dispersion Color Test.

6. A dispersion, comprising:
   (1) the zinc oxide particles of claim 1,
   (2) a liquid carrier, and
   (3) optionally an antioxidant.

7. The dispersion of claim 6, comprising the antioxidant, wherein the antioxidant is selected form the group consisting of vitamins, antioxidant minerals, antioxidant proteins, antioxidant enzymes, antioxidant coenzymes, phytonutrients and antioxidant hormones.

8. The dispersion of claim 6, wherein (1) the liquid carrier is a cosmetically acceptable liquid carrier, (2) the liquid carrier comprises a member selected from the group consisting of alkyl benzoates, fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

9. Zinc oxide particles having average particle size of 10 to 300 nm, wherein:
   the particles are stoichiometric zinc oxide,
   the particles have a ΔE value of at most 10 in a DPPH Photocatalytic Stability Test, and
   the particles have a ΔE value of at least 15 in a Dispersion Color Test;
   wherein the ΔE value in the DPPH Photocatalytic Stability Test is calculated as:

$$\Delta E = \sqrt{(L_2^* - L_1^*)^2 + (\alpha_2^* - \alpha_1^*)^2 + (b_2^* - b_1^*)^2},$$

wherein $L_2^*$, $\alpha_2^*$, and $b_2^*$ are the color coordinates of a zinc oxide particle test mixture post irradiation and where $L_1^*$, $\alpha_1^*$, and $b_1^*$ are the initial color coordinates of the zinc oxide particle test mixture prior to irradiation; and
   wherein the ΔE in the Dispersion Color Test is calculated as:

$$\Delta E = \sqrt{(L_2^* - L_1^*)^2 + (\alpha_2^* - \alpha_1^*)^2 + (b_2^* - b_1^*)^2},$$

wherein $L_2^*$, $\alpha_2^*$, and $b_2^*$ are the color coordinates of a zinc oxide particle test sample and wherein $L_1^* = 99.47$, $\alpha_1^* = -0.16$, and $b_1^* = -0.17$ correspond to color coordinates of a white reference tile.

10. A dispersion, comprising:
    (1) the zinc oxide particles of claim 9,
    (2) a liquid carrier, and
    (3) optionally an antioxidant.

11. The dispersion of claim 10, comprising the antioxidant, wherein the antioxidant is selected form the group consisting of vitamins, antioxidant minerals, antioxidant proteins, antioxidant enzymes, antioxidant coenzymes, phytonutrients and antioxidant hormones.

12. The dispersion of claim 11, wherein (1) the liquid carrier is a cosmetically acceptable liquid carrier, (2) the liquid carrier comprises a member selected from the group consisting of alkyl benzoates. fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

13. The dispersion of claim 10, wherein (1) the liquid carrier is a cosmetically acceptable liquid carrier, (2) the liquid carrier comprises a member selected from the group consisting of alkyl benzoates, fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

14. Coated particles, comprising:
    (a) zinc oxide particles, having:
       (i) an O:Zn ratio of at least 0.99, and
       (ii) a sufficient concentration of oxygen vacancies and zinc vacancies to give a dispersion of the particles in C12-C15 alkyl benzoate an orange to tan color corresponding to a ΔE value of at least 15 in a Dispersion Color Test, and
    (b) a silica coating, on the zinc oxide particles;
    wherein the coated particles have an average particle size of 10 to 300 nm;
    wherein the ΔE in the Dispersion Color Test is calculated as:

$$\Delta E = \sqrt{(L_2^* - L_1^*)^2 + (\alpha_2^* - \alpha_1^*)^2 + (b_2^* - b_1^*)^2},$$

wherein $L_2^*$, $\alpha_2^*$, and $b_2^*$ are the color coordinates of a zinc oxide particle test sample and wherein $L_1^* = 99.47$, $\alpha_1^* = -0.16$, and $b_1^* = -0.17$ correspond to color coordinates of a white reference tile; and
    wherein the coated particles contain no aggregates and have no detectable particles 500 nm or larger, on a number-weighted basis.

15. The coated particles of claim 14, wherein the silica coating is present in an amount of 0.5 to 40% by weight of the coated particles.

16. Multilayer coated particles, comprising:
    (I) the coated particles of claim 14, and
    (II) an organic moiety-containing coating, on the coated particles.

17. The multilayer coated particles of claim 16, wherein the organic moiety-containing coating is prepared by reacting the particles with at least member selected from the group consisting of a phosphatide, lecithin, a fatty alcohol and a glycerol ester.

18. A dispersion, comprising:
    (1) the coated particles of claim 14,
    (2) a liquid carrier, and
    (3) optionally an antioxidant.

19. The dispersion of claim 18, wherein (1) the liquid carrier is a cosmetically acceptable liquid carrier, (2) the liquid carrier comprises a member selected from the group consisting of alkyl benzoates, fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

20. The dispersion of claim 18, comprising the antioxidant, wherein the antioxidant is selected form the group consisting of vitamins, antioxidant minerals, antioxidant proteins, antioxidant enzymes, antioxidant coenzymes, phytonutrients and antioxidant hormones.

21. The dispersion of claim 20, wherein (1) the liquid carrier is a cosmetically acceptable liquid carrier, (2) the liquid carrier comprises a member selected from the, group consisting of alkyl benzoates, fatly acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

22. A dispersion, comprising:
    (1) the multilayer coated particles of claim 16,
    (2) a liquid carrier, and
    (3) optionally an antioxidant.

23. The dispersion of claim 22, comprising the antioxidant, wherein the antioxidant is selected form the group consisting of vitamins, antioxidant minerals, antioxidant proteins, antioxidant enzymes, antioxidant coenzymes, phytonutrients and antioxidant hormones.

24. The dispersion of claim 23, wherein (1) the liquid carrier is a cosmetically acceptable liquid carrier, (2) the liquid carrier comprises a member selected from the group consisting of alkyl benzoates, fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

25. The dispersion of claim 22, wherein (1) the liquid carrier is a cosmetically acceptable liquid carrier, (2) the liquid carrier comprises a member selected from the group consisting of alkyl benzoates, fatty acid esters, natural product oils, silicone oils and mixtures thereof; and/or (3) the liquid carrier comprises a member selected from the group consisting of ethyl benzoates, linear alkyl benzoate, capric/caprylic triglyceride and mixtures thereof.

26. Coated particles, comprising:
   (a) zinc oxide particles, having:
      (i) an O:Zn ratio of at least 0.99, and
      (ii) a sufficient concentration of oxygen vacancies and zinc vacancies to give a dispersion of the particles in C12-C15 alkyl benzoate an orange to tan color corresponding to a ΔE value of at least 15 in a Dispersion Color Test, and
   (b) an organic moiety-containing coating, on the zinc oxide particles,
   wherein the ΔE in the Dispersion Color Test is calculated as:

$$\Delta E = \sqrt{(L_2^* - L_1^*)^2 + (\alpha_2^* - \alpha_1^*)^2 + (b_2^* - b_1^*)^2},$$

wherein $L_2^*$, $\alpha_2^*$, and $b_2^*$ are the color coordinates of a zinc oxide particle test sample and wherein $L_1^* = 99.47$, $\alpha_1^* = -0.16$, and $b_1^* = -0.17$ correspond to color coordinates of a white reference tile;
   wherein the coated particles have an average particle size of 10 to 300 nm, and
   wherein the coated particles contain no aggregates and have no detectable particles 500 nm or larger, on a number-weighted basis.

27. The coated particles of claim 26, wherein the organic moiety-containing coating is prepared by reacting the particles with lecithin.

28. A method of protecting skin from light, comprising coating skin with the zinc oxide particles of claim 1.

29. A method of protecting keratinous material comprising coating the keratinous material with the zinc oxide particles of claim 1.

30. A method of protecting human skin comprising coating skin with the zinc oxide particles of claim 1.

31. A method of suppressing lipid peroxidation comprising applying to the skin the zinc oxide particles of claim 1.

32. A method of reducing lines and wrinkles on the skin comprising applying to the skin the zinc oxide particles of claim 1.

33. A method of inhibiting loss of elasticity of the skin comprising applying to the skin the zinc oxide particles of claim 1.

34. A method of inhibiting thinning of the skin comprising applying to the skin the zinc oxide particles of claim 1.

35. A method of protecting antioxidants, comprising mixing an antioxidant with the zinc oxide particles of claim 1.

* * * * *

UNITED STATES PATENT AND TRADEMARK OFFICE
CERTIFICATE OF CORRECTION

PATENT NO. : 11,672,744 B2
APPLICATION NO. : 17/186518
DATED : June 13, 2023
INVENTOR(S) : Harry W. Sarkas et al.

Page 1 of 1

It is certified that error appears in the above-identified patent and that said Letters Patent is hereby corrected as shown below:

In the Claims

Column 28, Line 42, at the beginning of the equation, please delete "$(L_2^*-L_1^*)$" and insert --$(L_2^*-L_1^*)^2$--

Signed and Sealed this
Nineteenth Day of August, 2025

Coke Morgan Stewart
*Acting Director of the United States Patent and Trademark Office*